Figure 1:
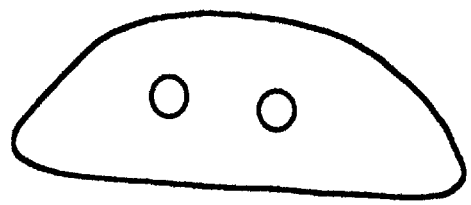

United States Patent [19]
Chen

[11] Patent Number: 6,161,555
[45] Date of Patent: Dec. 19, 2000

[54] CRYSTAL GELS USEFUL AS DENTAL FLOSS WITH IMPROVED HIGH TEAR, HIGH TENSILE, AND RESISTANCE TO HIGH STRESS RUPTURE PROPERTIES

[75] Inventor: John Young-Fu Chen, Pacifica, Calif.

[73] Assignee: Applied Elastomerics, Inc., South San Francisco, Calif.

[21] Appl. No.: 09/230,940

[22] PCT Filed: Sep. 30, 1997

[86] PCT No.: PCT/US97/17534

§ 371 Date: Feb. 3, 1999

§ 102(e) Date: Feb. 3, 1999

[87] PCT Pub. No.: WO98/14133

PCT Pub. Date: Apr. 9, 1998

Related U.S. Application Data

[63] Continuation-in-part of application No. 08/719,817, Sep. 30, 1996, which is a continuation-in-part of application No. 08/655,343, Jun. 17, 1996, and a continuation-in-part of application No. 08/612,586, Mar. 8, 1996, and a continuation-in-part of application No. 08/581,125, Dec. 29, 1995, Pat. No. 5,962,572, and a continuation-in-part of application No. 08/581,191, Dec. 29, 1995, Pat. No. 5,760,117, which is a continuation-in-part of application No. 08/581,188, Dec. 29, 1995, abandoned, and a continuation-in-part of application No. 08/288,690, Aug. 11, 1994, Pat. No. 5,633,286, and a continuation-in-part of application No. PCT/US94/07314, Jun. 27, 1994, and a continuation-in-part of application No. PCT/US94/04278, Apr. 19, 1994.

[51] Int. Cl.[7] .................................................. A61C 15/00
[52] U.S. Cl. ......................... 132/321; 132/323; 132/329
[58] Field of Search ................................. 132/321, 323, 132/329; 524/474, 476, 490, 505; 525/95, 89

[56] References Cited

U.S. PATENT DOCUMENTS

| | | | |
|---|---|---|---|
| 3,660,849 | 5/1972 | Jonnes | ........................................... 2/2.1 |
| 3,821,148 | 6/1974 | Makowski . | |
| 3,821,149 | 6/1974 | Makowski | ............................... 260/30.6 |
| 3,827,999 | 8/1974 | Crossland | ............................... 260/33.6 |
| 3,860,013 | 1/1975 | Czapor | ..................................... 132/91 |
| 4,136,699 | 1/1979 | Collins | .................................... 128/290 |
| 4,151,057 | 4/1979 | St. Clair . | |
| 4,176,240 | 11/1979 | Sabia | ......................................... 174/23 |
| 4,259,540 | 3/1981 | Sabia . | |
| 4,351,913 | 9/1982 | Patel . | |
| 4,361,508 | 11/1982 | Bourland | ................................ 523/173 |

(List continued on next page.)

FOREIGN PATENT DOCUMENTS

| | | |
|---|---|---|
| WO 88/00603 | 1/1988 | WIPO . |
| WO 90/05166 | 5/1990 | WIPO . |
| WO 91/05014 | 4/1991 | WIPO . |
| WO 93/05113 | 3/1993 | WIPO . |
| WO 93/23472 | 11/1993 | WIPO . |

OTHER PUBLICATIONS

"Styrene–Diene Triblock Copolymers: Orientation Conditions and Mechanical Properties of the Oriented Materials" A. Weill and R. Pixa, Journal of Polymer Science Polymer Symposium 58, 381–394 (1977).

Tuftec Trade Literature, Asani Chemical Co., Ltd., Synthetic Rubber Division, English and Japanese 14 Pages.

Septon Trade Literature, Kuraray Co., Ltd. 1995.8 (4,000) 15 Pages.

(List continued on next page.)

*Primary Examiner*—Gene Mancene
*Assistant Examiner*—Pedro Philogene

[57] ABSTRACT

A novel dental floss and gum massager made in the form of a strand, a tape or a sheet of polymeric material, said sheet having selectively positioned multiple sized holes for inserting though and holding by the fingers of the hands. The floss provides substantially very little constriction of blood flow surrounding the fingers as the floss is held taught and the peripheral edge of the floss is being manipulated and worked by the gripping, pulling, pushing, deforming, and guilding back and forth actions of the fingers during massaging of the gums and flossing of the teeth.

14 Claims, 2 Drawing Sheets

U.S. PATENT DOCUMENTS

| | | | |
|---|---|---|---|
| 4,369,284 | 1/1983 | Chen | 524/476 |
| 4,432,607 | 2/1984 | Levy | 350/96.34 |
| 4,450,849 | 5/1984 | Cerceo et al. | 132/321 |
| 4,492,428 | 1/1985 | Levy . | |
| 4,497,538 | 2/1985 | Patel . | |
| 4,509,821 | 4/1985 | Stenger | 350/96.23 |
| 4,600,261 | 7/1986 | Debbaut . | |
| 4,610,738 | 9/1986 | Jervis | 156/49 |
| 4,618,213 | 10/1986 | Chen | 524/476 |
| 4,643,924 | 2/1987 | Uken | 428/35 |
| 4,662,692 | 5/1987 | Uken | 339/96 |
| 4,678,664 | 7/1987 | Schmolka | 424/65 |
| 4,680,233 | 7/1987 | Camin | 428/424.6 |
| 4,690,831 | 9/1987 | Uken | 427/44 |
| 4,692,369 | 9/1987 | Nomi | 428/198 |
| 4,709,982 | 12/1987 | Corne | 427/44 |
| 4,716,183 | 12/1987 | Gamarra | 522/90 |
| 4,721,832 | 1/1988 | Toy | 174/87 |
| 4,764,535 | 8/1988 | Leicht . | |
| 4,798,853 | 1/1989 | Handlin | 523/173 |
| 4,801,346 | 1/1989 | Huddleston . | |
| 4,822,834 | 4/1989 | Blevins | 524/427 |
| 4,833,193 | 5/1989 | Sieverding . | |
| 4,842,931 | 6/1989 | Zook | 428/354 |
| 4,864,725 | 9/1989 | Debbaut | 29/871 |
| 4,865,905 | 9/1989 | Uken | 428/220 |
| 4,880,676 | 11/1989 | Pulgcerver | 428/35.7 |
| 4,880,878 | 11/1989 | Himes | 525/89 |
| 4,883,431 | 11/1989 | Uken . | |
| 4,888,070 | 12/1989 | Clark . | |
| 4,889,171 | 12/1989 | Covington | 428/304 |
| 4,889,403 | 12/1989 | Zucker . | |
| 4,900,877 | 2/1990 | Dubrow | 174/35 |
| 4,909,756 | 3/1990 | Jervis . | |
| 4,929,211 | 5/1990 | Resnick | 446/14 |
| 4,942,270 | 7/1990 | Gamarra | 174/93 |
| 4,944,363 | 7/1990 | Osher | 273/58 |
| 4,944,973 | 7/1990 | Follette . | |
| 4,968,747 | 11/1990 | Mallikarjun | 525/74 |
| 4,983,008 | 1/1991 | Campbell | 350/96.16 |
| 5,026,054 | 6/1991 | Osher | 273/58 |
| 5,059,748 | 10/1991 | Allen | 174/87 |
| 5,068,138 | 11/1991 | Mitchell | 428/36.8 |
| 5,085,597 | 2/1992 | Story | 439/521 |
| 5,088,734 | 2/1992 | Glava | 273/73 |
| 5,098,421 | 3/1992 | Zook | 604/367 |
| 5,126,182 | 6/1992 | Douglas | 428/90 |
| 5,149,736 | 9/1992 | Gamarra | 524/490 |
| 5,153,254 | 10/1992 | Chen | 524/505 |
| 5,159,022 | 10/1992 | Ikematu | 525/250 |
| 5,167,649 | 12/1992 | Zook | 604/307 |
| 5,173,573 | 12/1992 | Jervis | 174/138 |
| 5,177,143 | 1/1993 | Toy | 524/848 |
| 5,181,914 | 1/1993 | Zook | 604/307 |
| 5,191,752 | 3/1993 | Murphy | 54/44.5 |
| 5,221,534 | 6/1993 | Deslauriers | 424/78.03 |
| 5,239,723 | 8/1993 | Chen | 15/104 |
| 5,262,468 | 11/1993 | Chen | 524/476 |
| 5,313,019 | 5/1994 | Brusselmans | 174/93 |
| 5,324,222 | 6/1994 | Chen | 446/34 |
| 5,330,452 | 7/1994 | Zook | 604/307 |
| 5,334,646 | 8/1994 | Chen | 524/474 |
| 5,336,708 | 8/1994 | Chen | 524/474 |
| 5,459,193 | 10/1995 | Anderson | 524/505 |
| 5,475,890 | 12/1995 | Chen | 15/104 |
| 5,479,952 | 1/1996 | Zachariades | 132/321 |
| 5,508,334 | 4/1996 | Chen | 524/474 |
| 5,559,165 | 9/1996 | Paul | 523/111 |
| 5,606,149 | 2/1997 | Yaworski | 174/92 |
| 5,618,882 | 4/1997 | Hammond et al. | 525/89 |
| 5,624,294 | 4/1997 | Chen | 446/253 |
| 5,626,657 | 5/1997 | Pearce | 106/122 |
| 5,633,286 | 5/1997 | Chen | 524/474 |
| 5,655,947 | 8/1997 | Chen | 446/46 |
| 5,863,977 | 1/1999 | Fisher . | |
| 5,872,201 | 2/1999 | Cheung . | |
| 5,929,138 | 7/1999 | Mercer . | |
| 5,952,396 | 9/1999 | Chang | 522/1 |
| 5,994,446 | 11/1999 | Graykys . | |
| 5,994,450 | 11/1999 | Pearce | 524/505 |

OTHER PUBLICATIONS

Shell Chemical Co., Data Sheets: EKP–207 (093094–02) and L–1203 (SC:2384–950.

SC:1102–89 Shell Chemical Technical Bulletin "Kraton®Thermoplastic Rubber in Oil Gels", Apr. 1989.

"Tuftec"—its characteristics and applications, Assahi Chemical.

Septon, High Performance Thermoplastic Rubber, Kurraray Co., Ltd., 1995.

Kraton Polymers, May 1997, Shell Chemical Company.

Silipos product catlouge.

Silipos products catlouge sheets: Silosheath, Pressure Ulcers,Friction Sleeves with Gel, Gel–E–Rol & Friction Tape, Mesh Tubing,Silopad.

Silipos manual, 1994.

*Melt Miscibility In Blends Of Polypropylene, Polystryenhe–Block–Poly (Ethylene–Sat–Butylene)–Block–Polystyrene, and Processing Oil From Melting Point Depression*, Ohlesson et al., Polymer Engineering and Science, 1996, vol. 36, No. 11.

*Blends And Thermoplastic Interpenetrating Polymer Networks Of Polypropytlene And Polystyrene–Block–Poly(Ethylene–Stat–Butylene)–Block–Polytstyrene Triblock Copolymer. 1: Morphology And Structure–Related Pproperties* , Ohlesson, et al., Polymer Engineering and Science, Feb. 1996, vol. 36, No.4.

*Migration And Blooming Of Waxes To The Surface Of Rubber Vulcanizates*, Nah, et al., J. Of Polymer Science: Polymer Physics Ed., vol. 18, 511–521 (1980).

"SiloLiner" Sales literature from Knit–Rite medical (Mar. 1, 1999 three pages).

ALPS South Corporation–Gel Liners: NEW!Easy Liner ELPX, ELDT and ELFR published fact sheet downloaded from the Internet on Aug. 10, 1999.

Chung P. Park and George P. Clingerman, "Compatibilization of Polyethylene–Polystyrene Blends with Ethylene–Styrene Random Copolymers", the Dow Chemical Company, May 1996.

Steve Hoenig, Bob Turley and Bill Van Volkenburgh, "Material Properties and Applications of Ethylene–Styrene Interpolymers", the Dow Chemical Company, Sep. 1996.

Y. Wilson Cheung and Martin J. Guest, "Structure, Thermal Transitions and Mechanical Properties of Ethylene/Styrene Copolymers", the Dow Chemical Company, May 1996. (17).

Teresa Plumley Karjaia, Y. Wilson Cheung and Martin J. Guest, "Melt Rheology and Processability of Ethylene/Styrene Interpolymers", the Dow Chemical Company, May 1997.

D. C. Prevorsek, et al., Origins of Damage Tolerance in Ultrastrong Polyethylene Fibers and Composites:, Journal of Polymer Science: Polymer Symposia No. 75, 81–104 (1993).

Chen, H., et al, "Classification of Ethylene–Styrene Interpolymers Based on Comonomer Content", J. Appl. Polym. Sci., 1998, 70, 109.

Alizadeh, et al., "Effect of Topological Constraints on The Crystallization Behavior of Ethylene/allpha–Olefin Copolymers", PMSE, vol. 81, pp. 248–249, Aug. 22–26, 1999.

Guest, et al., "Structre/Property Relationships of Semi–Crystalline Ethylene–Styrene Interpolymers (ESI)", PMSE, vol. 81, pp. 371–372, Aug. 22–26, 1999.

CRYSTAL GELS USEFUL AS DENTAL FLOSS WITH IMPROVED HIGH TEAR, HIGH TENSILE, AND RESISTANCE TO HIGH STRESS RUPTURE PROPERTIES

ORIGINS OF INVENTION AND RELATED APPLICATIONS

This application is a continuation-in-part application of copending application No. 08/719,817 filed Sep. 30, 1996, which is a CIP of Ser. No. 08/665,343 filed Jun. 17, 1996 and a CIP of Ser. No. 08/612,586 filed Mar. 8, 1996 and a CIP of No. 08/581,125 filed Dec. 29, 1995, (now Pat. No. 5,962,572) and also a CIP of No. 08/581,191 filed Dec. 29, 1995, now U.S. Pat. No. 5,760,117 issued Jun. 2, 1998. This application is also a CIP of Ser. No. 08/581,188 filed Dec. 29, 1995, now abandoned and a CIP of Ser. No. 08/288,690 filed Aug. 11, 1994, now U.S. Pat. No. 5,633,286 and also a CIP of PCT/US94/07314 filed Jun. 27, 1994, and a CIP of PCT/US94/04278, filed Apr. 19, 1994. The subject matter contained in the related application is specifically incorporated herein by reference.

TECHNICAL FIELD OF THE INVENTION

The present invention relates to dental floss and gum massager.

BACKGROUND ART

Thermoplastic elastomer SEBS gels are described in Pat. Nos. 5,334,646, 5,508,334, 5,262,468, 5,153,254, 4,618,213; and 4,369,284. These gels can be use for flossing because of their extreme softness and strength. The SEBS and SEPS triblock copolymer oil gels, however, do not have sufficient resistance to tearing when the gel is repeatedly notched or nicked by inserting and re-inserting between the teeth gaps while at the same time applying constant tension to the floss. This failure makes triblock copolymer gels much less desirable and commercially useless and unacceptable to the flossing consumer.

DISCLOSURE OF INVENTION

1. Statement Of The Invention

I have discovered an improved dental floss and gum massager made from novel compositions comprising gels with improved high tear strength, improved high tensile strength, and improved resistance to high stress rupture. The improved gels can be formed into gel strands, gel tapes, and gel sheets for massaging the gum and flossing the teeth. The gel floss can be in the form of strands and tapes when rapped around the fingers for holding, extending, and flossing are advantageously more comfortable and less restricting to blood circulation in the fingers than conventional dental floss. When the gel floss is in the form of a sheet, it is additionally advantages for the sheet to have at least two separate selective sized holes at a selective distance apart for holding said sheet by one or more fingers of one or both hands, said sheet having a selected shaped peripheral sheet edge of a selective thickness, said holes being a selective distance from said edge and sized for insertion through by at least one said finger of each hand for holding said sheet and gripping, pulling, pushing, deforming, working, deforming, manipulating, folding and guilding said sheet edge for massaging the gum and flossing the teeth without substantial constriction of blood flow of said fingers by said sheet.

I have now discovered gels with improved damage tolerance, crack propagation resistance and tear resistance which are advantageously suitable for use as dental floss that are from about twice to about ten times or better in lowering the gap insertion breaking frequency than same rigidity gels made from triblock copolymer oil gels alone.

The invention comprises gels and articles useful as floss made from mixtures of triblock copolymers having at least one different midblock or multiblock copolymers having one, two or more different midblocks which gels exhibit advantages of improved tensile strength, improved tear strength (propagation resistance under tension and continuous notching and nicking) and additionally improved resistance to high stress rupture. Such combination of properties are not found in gels of substantially the same rigidity made from SEBS or SEPS triblock copolymers alone. The gels of the present invention exhibit low set, high dimensional stability, crack, tear, craze, and creep resistance under tension, excellent tensile strength and high elongation, long service life under shear, stress and strain and capable of withstanding repeated dynamic shear, tear and stress forces, excellent processing ability for cast molding, extruding, fiber forming film forming and spinning, non-toxic, nearly tasteless and odorless, soft and strong, optically clear, highly flexible, possessing elastic memory, substantially with little or no plasticizer bleedout. The gels are especially advantageously suitable where resistance to crazing, cracking, fracturing, and catastrophic failure while under dynamic stretch tension loads in an environment where continuous or repeated shearing, cutting, nicking, notching, lacerating, mutilating, and tearing of the gel in contact with or between other bodies (i.e., abraded by repeated contact with another body or bodies) are encountered, such as those forces acting during dental flossing. The resistance to tear propagation or ability to stop direct crack propagation under dynamic tension loads is a critical factor and an advantage of the present gels over triblock copolymer gels alone.

Still further, the tear resistance of gels floss based on typical SEBS or SEPS triblock copolymers can be improved with the addition of the multiblock copolymers or selected crystalline block copolymers forming the gels of the invention.

Generally, the instant improved gels comprises: (I) 100 parts by weight of one or more high viscosity or selected low viscosity linear, branched, radial, star-shaped, multi-arm or branched block copolymers or mixtures of two or more such block copolymers, said block copolymers having one or more midblocks, said midblocks comprising one or more substantially amorphous midblocks or one or more substantially crystalline polyethylene midblocks and with nil, one or more amorphous midblocks with the proviso that when said gel comprises a mixture of one or more of a substantially amorphous midblock block copolymers, at least one selected substantially crystalline polyethylene midblock block copolymer is present in combination in said admixture; optionally in combination with a selected amount of one or more of a (II) polymer or copolymer, and selected amounts of a plasticizing oil (III) sufficient to achieve gel rigidities of from less than about 2 gram Bloom to about 1,800 gram Bloom with the proviso that said block copolymers having nil amorphous midblocks are combined with at least one block copolymer having at least one amorphous midblock.

As used herein, the term "gel rigidity" in gram Bloom is determined by the gram weight required to depress a gel a distance of 4 mm with a piston having a cross-sectional area of 1 square centimeter at 23° C.

The gels comprising thermoplastic elastomer block copolymers having one or more advantageously sufficient amount of crystalline polyethylene midblocks of the invention are hereafter referred to as "elastic-crystalline gels" or simpler "crystal gels". The block midblocks of copolymers forming the crystal gels of the invention are characterized by sufficient crystallinity as to exhibit a melting endotherm of at least about 40° C. as determined by DSC curve.

The various types of high viscosity or low viscosity linear, branched, radial, star-shaped or multiarm block copolymers or mixtures of two or more such block copolymers employed in forming the crystal gels of the invention are of the general configurations A-Z-A and $(A-Z)_n$, wherein the subscript n is two or more. In the case of multiarm block copolymers where n is 2, the block copolymer denoted by $(A-Z)_n$ is A-Z-A. It is understood that the coupling agent is ignored for sake of simplicity in the description of the $(A-Z)_n$ block copolymers.

The end block segment (A) comprises a glassy amorphous polymer end block segment, preferably, polystyrene. The midblocks (Z) comprises one or more midblocks of substantially poly(butylene) or -B- as further denoted below and substantially crystalline poly(ethylene) (simply denoted by "-E- or (E)") with or without one or more amorphous midblocks of poly(butylene), poly(ethylene-butylene), poly(ethylene-propylene) or combination thereof (the amorphous midblocks are denoted by "-B- or (B)", "-EB- or (EB)", and "-EP- or (EP)" respectively or simply denoted by "-W- or (W)" when referring to one or more of the amorphous midblocks as a group) The A and Z portions are incompatible and form a two or more-phase system consisting of sub-micron amorphous glassy domains (A) interconnected by (Z) chains. The glassy domains serve to crosslink and reinforce the structure. This physical elastomeric network structure is reversible, and heating the polymer above the softening point of the glassy domains temporarily disrupt the structure, which can be restored by lowering the temperature.

The (I) linear, branched, radial, star-shaped, multi-arm or branched block copolymers block copolymers are characterized as having a Brookfield Viscosity value at 5 weight percent solids solution in toluene at 30° C. of from less than about 40 cps to about 60 cps and higher, advantageously from about 40 cps to about 160 cps and higher, more advantageously from about 50 cps to about 180 cps and higher, still more advantageously from about 70 cps to about 210 cps and higher, and even more advantageously from about 90 cps to about 380 cps and higher.

The (I) linear, branched, radial, star-shaped, multi-arm or branched block copolymers are characterized as having a Brookfield Viscosity value at 5 weight percent solids solution in toluene at 30° C. of from about 80 cps to about 380 cps and higher, advantageously from about 150 cps to about 260 cps and higher, more advantageously from about 200 cps to about 580 cps and higher, and still more advantageously from about 100 cps to about 800 cps and higher.

The substantially amorphous block copolymers (SEBS or $(SEB)_n$ with high butylene content and SEPS or $(SEP)_n$ with high isopropylethyene content) forming components of mixtures of the gels of the present invention are of high molecular weights, but by their nature exhibit lower viscosity which advantageously range from less than about 1,000 cp to about 100 cp toluene viscosity at 10% solids at 25° C., more advantageously less than about 500 cp to about 100 cp, still more advantageously less than about 200 cp to about 90 cp or less.

The crystal gels can be made in combination with a selected amount of one or more selected polymers and copolymers (II) including thermoplastic crystalline polyurethane elastomers with hydrocarbon midblocks, homopolymers, copolymers, block copolymers, polyethylene copolymers, polypropylene copolymers, and the like described below.

The crystal gels forming the floss of the invention are also suitable in physically interlocking or forming with other selected materials to form gel composites combinations. The materials are selected from the group consisting of foam, plastic, fabric, various natural and synthetic resins particles, fibers and films.

Commercial resins which can aid in adhesion to materials (plastics, glass, and metals) may be added in minor amounts to the gelatinous elastomer composition, these resins include: polymerized mixed olefins (Super Sta-tac, Betaprene Nevtac, Escorez, Hercotac, Wingtack, Piccotac), polyterpene (Zonarez, Nirez, Piccolyte, Sylvatac), glycerol ester of rosin (Foral), pentaerythritol ester of rosin (Pentalyn), saturated alicyclic hydrocarbon (Arkon P), coumarone indene (Cumar LX), hydrocarbon (Picco 6000, Regalrez), mixed olefin (Wingtack), alkylated aromatic hydrocarbon (Nevchem), Polyalphamethylstyrene/vinyl toluene copolymer (Piccotex), polystyrene (Kristalex, Piccolastic), special resin (LX-1035), and the like.

Furthermore, the interlocking materials with the gel of the invention may be made from flexible materials, such as fibers and fabrics of cotton, flax, and silk. Other flexible materials include: elastomers, fiber-reinforced composites, mohair, and wool. Useful synthetic fibers include: acetate, acrylic, aremid, glass, modacrylic polyethylene, nylon, olefin, polyester, rayon, spandex, carbon, sufar, polybenzimidazole, and combinations of the above. Useful open-cell plastics include: polyamides, polyimides, polyesters, polyisocyanurates, polyisocyanates, polyurethanes, poly(vinyl alcohol), etc. Open-celled Plastic (foams) suitable for use with the compositions of the invention are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference. These include: open and non-opened cell silicone, polyurethane, polyethylene, neoprene, polyvinyl chloride, polyimide, metal, ceramic, polyether, polyester, polystyrene, polypropylene. Example of such foams are: Thanol®, Arcol®, Ugipol®, Arcel®, Arpak®, Arpro®, Arsan®, Dylite®, Dytherm®, Styrofoam®, Trymer®, Dow Ethafoam®, Ensolite®, Scotfoam®, Pyrell®, Volana®, Trocellen®, Minicel®, and the like.

The various aspects and advantages of the invention will become apparent to those skilled in the art upon consideration of the accompanying disclosure and the drawings.

FIGURES

FIG. 1. Representative sectional views of unexpanded gel floss of the invention.

Figure 2:
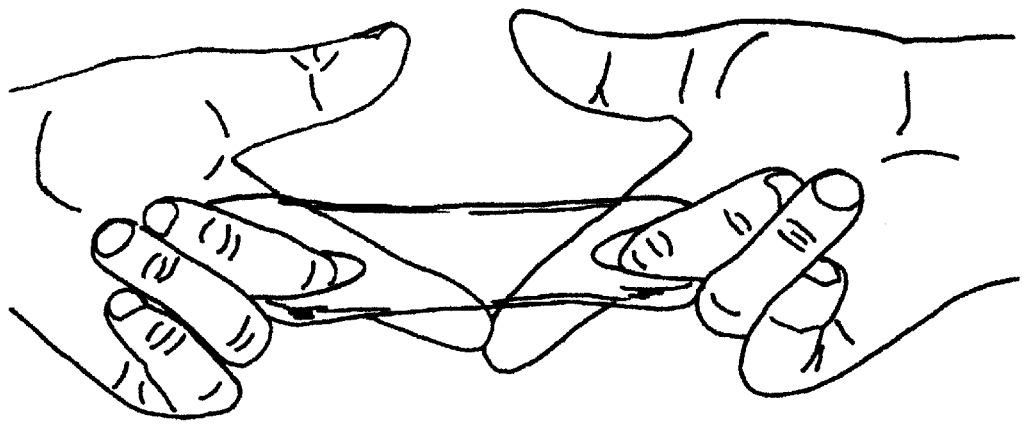

FIG. 2. Representative views of expanded gel floss of the invention.

Figure 3:
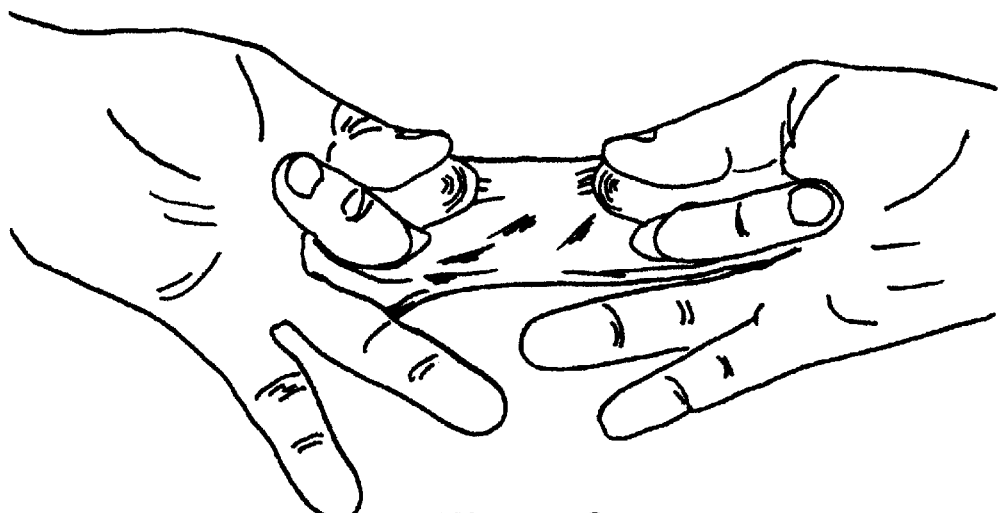

FIG. 3. Representative views of expanded gel floss of the invention.

Figure 4:
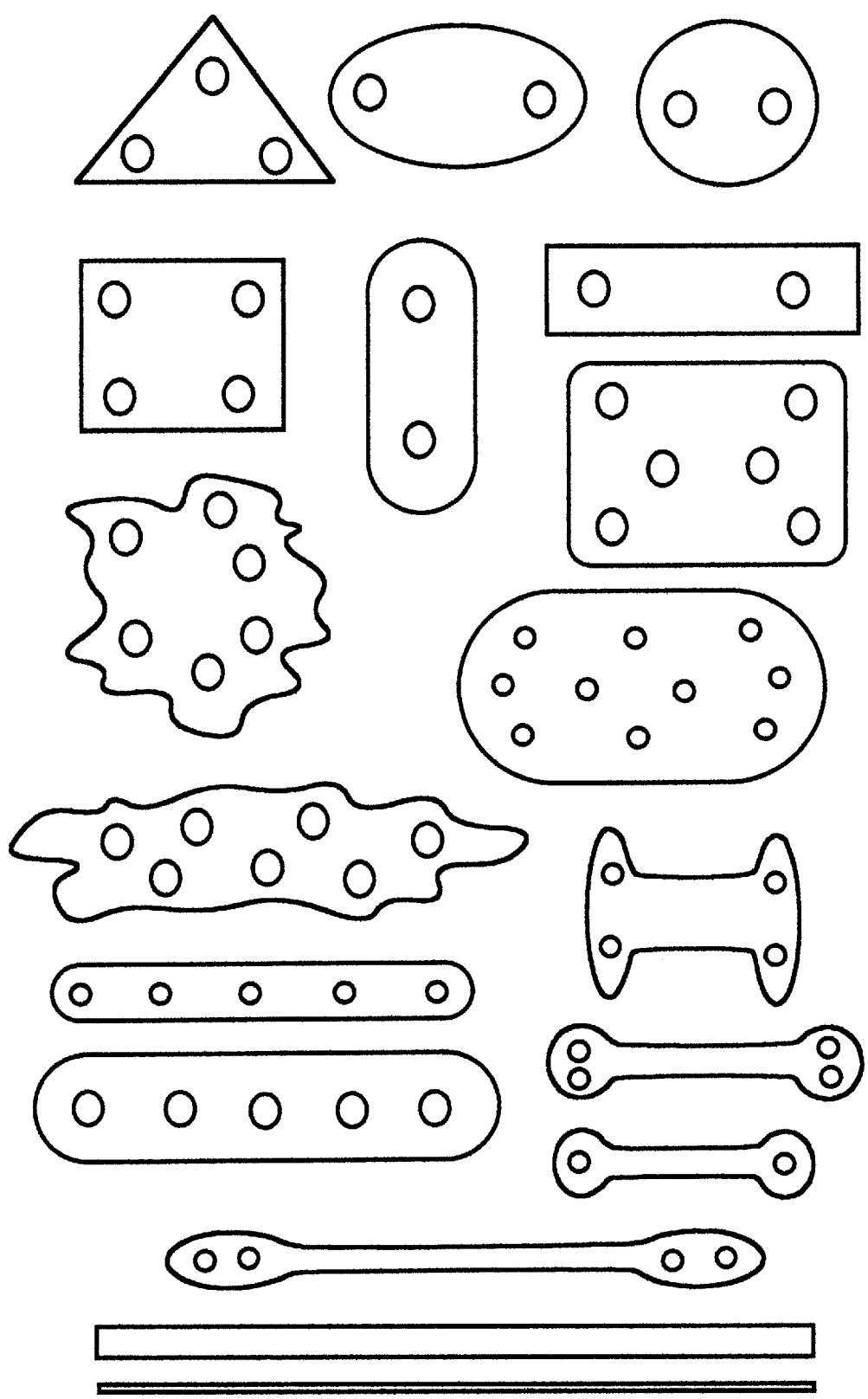

FIG. 4. Representative sectional views of various gel floss of the invention.

MODES FOR CARRYING OUT THE INVENTION

The process of flossing involve inserting a segment of the floss into each gap between the teeth, moving the floss with a up-and-down motion while holding it tightly in tension and rubbing the sides of each tooth down to the gum line to remove plaque. The main problem with conventional dental floss, such as waxed, unwaxed nylon, spongy nylon, and teflon is that when tension is applied while inserting it between the teeth, the floss can forcefully strike the gum or gum line as it is inserted through a tight teeth gap suddenly releasing with a snap, impacting the gum, producing pain, at times causing lacerations or bleeding of the gums. Another serious problem using conventional floss is that the tension applied in flossing is transferred to the floss windings around the fingers as the floss is pulled tightly in tension for insertion through the gap and in tension for up-and-down flossing. With the flossing of each teeth, the cumulative tensions cause the windings to become ever tighter. As with teflon floss, more windings are needed to maintain tension because of natural slippage. Without loosening of the windings, eventually, the fingers can become extremely uncomfortable turning blue from lack of circulation. With the use of conventional floss and teflon less so, shredding of the floss caused by tight teeth gaps is another problem. Up to now, the process of flossing can be an uncomfortable experience. People knowing they should floss do not or do not do so as often because of the pain and discomfort involved. Most dentist would not recommend young children to floss their own teeth because serious gum damage may result due to improper flossing.

Tearing of the SEES gels has been of major concern. In general, amorphous gels such as those made form SEES and SEPS can fail catastrophically when subjected repeatedly to applied forces of high dynamic and static deformations, such as extreme compression, torsion, high tension, high elongation involving tearing and high stress rupture conditions encountered during flossing. Additionally, the development of cracks or crazes resulting from a large number of deformation cycles can induce catastrophic fatigue failure of amorphous gel composites, such as tears and rips between the surfaces of the amorphous gel and substrates or at the interfaces of interlocking material(s) and gel. Consequently, such amorphous gels are inadequate for the most demanding applications involving endurance at high stress and strain levels over an extended period of time. Consequently, when the gel is used as floss which when cut or notched during use, the resulting catastrophic failure renders the gel floss useless. Therefore, the World needs a softer, gentler, more gum friendly non-lacerating dental floss.

Normally, for triblock copolymer gel floss, tensile stress, bending, or twisting are not the cause of failure; it is the crack openings, v-notches or nicks formed on opposite sides of the gel floss as it is inserted and re-inserted into the teeth gap under continuous tension that develops and fails catastrophically. It is observed that triblock copolymer gel floss break apart suddenly under tension during the first insertion, often times it can catastrophically break apart during the second or third insertion, and more often times it can catastrophically snap apart during the third or fourth insertions. In most instances, the triblock copolymer gel floss fail by the fourth or fifth insertions when inserted in a normal tight gap between normal front teeth and fail on the first or second insertions when used between facing tight contacting amalgam molars.

The reason why this happens is possibly that at the point where the gel floss is damaged (cut, notched or nicked) a craze front develops as more voids form along the line perpendicular to the floss' elongated direction (i.e., applied tension) resulting in sudden unstoppable fracturing of the bulk material ahead of the notched point causing complete catastrophic failure of the floss.

Consequentially, its very frustrating to attempt to floss a full set of upper or lower teeth with triblock copolymer gel floss. It is the complete, unstoppable catastrophic failure of the triblock copolymer gel floss in tension while being worked in the gap of the teeth that must be prevented in order for the gel to be useful for flossing.

Therefore, gels providing greater tear resistance under applied tension are needed before "gels" as a class of materials can be commercialized for use as dental floss. The gap insertion "breaking frequency" of the gel floss must be substantially lowered before the gel can be acceptable by the consumer for flossing. Breaking frequency means the number of flossing cycles to break of a floss where one cycle comprises an insertion and extraction a floss between the teeth gap.

Block copolymers with polyethylene midblocks alone do not form suitable gels for use in making the gels of the invention. Crystalline midblock regions needs to be balanced with amorphous midblock regions in order to obtain soft, flexible and elastic gels with the desired crystalline properties that are not found in typical SEBS and SEPS gels.

The polymers forming the gels of the invention comprises crystalline/glassy domain/amorphous structures which are described and illustrate in copending application No. 863, 794. Although the structure can be spheroid, cylinders and plates are also within the scope of the present invention. Cylinder and plate structure are obtained with increasing glassy A end blocks. From about 15–30% by weight of A blocks, the block copolymer structure is spheroid. From about 33 about 40% by weight of A blocks, the block copolymer structure becomes cylindrical; and above about 45% A blocks, the structure becomes less cylindrical and more plate like.

In order to obtain elastic crystal gels forming the floss of the invention, it is necessary that the selective synthesis of butadiene produce sufficient amounts of 1,4 poly(butadiene) that on hydrogenation can exhibit "crystallinity" in the midblocks. In order for the block copolymers forming the crystal gels of the invention to exhibit crystallinity, the crystalline midblock segments must contain long runs of —$CH_2$— groups. There should be approximately at least 16 units of —($CH_2$)— in sequence for crystallinity. Only the (—$CH_2$—)$_4$ units can crystallize, and then only if there are at least 4 units of (—$CH_2$—)$_4$ in sequence; alternatively, the polyethylene units are denoted by [—($CH_2$—$CH_2$—$CH_2$—$CH_2$)—]$_4$, [(—$CH_2$—)$_4$]$^4$ or (—$CH_2$—)$^{16}$. The amount of (—CH2—)$^{16}$ units forming the (E) midblocks of the block copolymers comprising the crystal gels of the invention should be at least about 20% which amount is capable of exhibiting a melting endotherm in differential scanning calorimeter (DCS) curves.

Advantageously, the elastomer midblock segment should have a crystallinity of at least about 20% of (—$CH_2$—)16 units of the total mole % forming the midblocks of the block copolymer, more advantageously at least about 25%, still more advantageously at least about 30%, especially advantageously at least about 40% and especially more advantageously at least about 50% and higher. Broadly, the crystallinity of the midblocks should range from at least about 20% to about 60%, less broadly from at least about 18% to about 65%, and still less broadly from at least 22% to about 70%.

The melting endotherm in DSC curves of the crystalline block copolymers comprising at least 20% crystallinity are much higher than conventional amorphous block copolymers. The maximum in the endotherm curves of the crystalline block copolymers occurs at about 40° C., but can range from greater than about 25° C. to about 60° C. and higher. The crystalline block copolymers forming the crystal gels of the invention can exhibit melting endotherms (as shown by DSC) of about 25° C. to about 75° C. and higher. More specific melting endotherm values of the crystalline midblock block copolymers include: about 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 90° C., 110° C., 120° C., and higher, whereas, the melting endotherm (DSC) for conventional amorphous midblock segment block copolymers are about 10° C. and lower.

The melting endotherm is seen on heating and a sharp crystallization exotherm is seen on cooling. Such midblock crystallization endothermic and exothermic characteristics are missing from DSC curves of amorphous gels. The crystallization exotherm and fusion endortherm of the crystalline block copolymer gels of the invention are determined by ASTM D 3417 method.

Generally, the method of obtaining long runs of crystalline —($CH_2$)— is by sequential block copolymer synthesis followed by hydrogenation. The attainment of crystal gels of the instant invention is solely due to the selective polymerization of the butadiene monomer (forming the midblocks) resulting in one or more predetermined amount of 1,4 poly(butadiene) blocks followed by sequential polymerization of additional midblocks and hydrogenation to produce one or more crystalline midblocks of the final block copolymers.

The crystalline block copolymers are made by sequential block copolymer synthesis, the percentage of crystallinity or (—$CH_2$—)$^{16}$ units should be at least about $(0.67)^4$ or about 20% and actual crystallinity of about 12%. For example, a selectively synthesized S-$EB_n$-S copolymer having a ratio of 33:67 of 1,2 and 1,4 poly(butadiene) on hydrogenation will result in a midblock with a crystallinity of $(0.67)^4$ or 20%. For sake of simplicity, when n is a subscript of -EB-, n denotes the percentage of (—CH2—)$_4$ units, eg, n=67 or 20% crystallinity which is the percentage of $(0.67)^4$ or "(—$CH_2$—)$^{16}$" units. Thus, when n=28 or 72% of (—$CH_2$—)$_4$ units, the % crystallinity is $(0.72)^4$ or 26.87% crystallinity attributed to (—$CH_2$—)$_{16}$ units, denoted by -$EB_{28}$-. As a matter of convention, and for purposes of this specification involving hydrogenated polybutadiene: the notation -E- denotes at least about 85% of (—$CH_2$—)$_4$ units. The notation -B- denotes at least about 70% of [—$CH_2$—CH($C_2H_5$)—] units. The notation -EB- denotes between about 15 and 70% [—$CH_2$—CH($C_2H_5$)—] units. The notation -$EB_n$— denotes n % [—$CH_2$—CH($C_2H_5$)—] units. For hydrogenated polyisoprene: The notation -EP- denotes about at least 90% [—$CH_2$—CH($CH_3$)—$CH_2CH_2$—] units. The notation -P- denotes about at least greater than about 70% polyisopropylethyene units.

Likewise, in order to obtain the highly amorphous midblock components such as -B- forming the elastic gels of the floss of the invention, it is necessary that the selective synthesis of butadiene produce sufficient amounts of vinyl or 1,2 poly(butadiene) that on hydrogenation can exhibit "substantially amorphous polybutene" midblocks. The notation -B- denotes greater than above about 70% [—$CH_2$—CH($C_2H_5$)—]$_n$ polybutene units and -P- denotes greater than about 70% [—CH(CH—$2CH_3$)—$CH_2$—]$_n$ polyisopropyl-ethyene units. The substantially amorphous midblocks -$EB_n$- and -$EP_n$- of $SEB_nS$ and $SEP_nS$ (or more simply denoted when n % is greater than about 70% as -B- and -P-) are more advantageously when n % is greater than about 75%, still more advantageously greater than about 80%, and still more advantageously greater than about 85%, and even still more advantageously greater than about 90% or higher. Typically, high polybutene content $SEB_nS$ or simply SBS is made by adding structure modifiers, such as ethers, which gives more 1,2 polybutadiene and after hydrogenation, more polybutene, resulting in less crystallinity, softer block copolymer, lower viscosity, and higher $T_g$. Likewise, high polyisopropylethyene content $SEP_nS$ or simply S-P-S is made by adding structure modifiers to give more 3,4 structure and after hydrogenation, more polyisopropylethyene, resulting in softer block copolymer, lower viscosity, and higher $T_g$.

The major advantages of $SEB_nS$ and $SEP_nS$ over SEBS, SEPS (when n % greater=than about 70%) is the $T_g$ of poly(styrene-ethylene-butylene$_{>70}$-styrene) and poly(styrene-ethylene/propylene-isopropylethyene$_{>70}$-styrene) are much higher; the gel rigidities are lower; and the viscosities are much lower. More specifically, the Tg of SEBS is typically about −58° C. and the Tg of SEPS is typically about −50° to about −60° C. Whereas, the Tg of $SEB_nS$ and $SEP_nS$ with high butylene content and high isopropylethyene content can be advantageously much higher of about less than about −40° C., advantageously −30° C. and more advantageously higher of about −27° C. and higher.

It is extraordinary that where typical SEBS and SEPS gels fails to provide adequate tensile strength, fails to provide adequate tear strength, and fails to provide adequate resistance to high stress rupture suitable for use as dental floss, hereto unknown and unappreciated modification of the midblock structures provide heretofore unrealizable improved higher tensile strength, improved higher tear strength, and improved higher resistance to high stress rupture.

Theory notwithstanding, SEBS and SEPS gels fail to provide adequate properties for use as dental floss. The following is known:

i) gels made from typical SEBS which is created from a mixture of 1, 4- and 1,2-polybutadiene to provide a random mixture of ethylene and butylene units adequate to suppress crystallinity (as noted by Legge). Such gels can not provide adequate tear strength and lack adequate resistance to high stress rupture.

ii) gels made from typical SEPS which is created by hydrogenation of cis-1,4-polyisoprene results in a 1:1 ethylene/propylene elastomer midblock (as noted by Legge). Such gels can not provide adequate tear strength and lack adequate resistance to high stress rupture.

Contrary to the inferior properties of the above gels 1) and 2), the following gels are found to be superior and of improved high tear strength, improved resistance to high stress rupture and sufficient adequate tensile strength for use as dental floss:

iii) gels made from an admixture of a high crystalline ethylene content S-$E_n$B-S block copolymer and a high butylene content S-$EB_n$-S block copolymer.

iv) gels made from an admixture of a high crystalline ethylene content S-$E_n$B-S block copolymer and a high polyisopropylethyene content S-$EP_n$-S block copolymer.

v) gels made from an admixture of a high crystalline ethylene content S-$E_n$B-S block copolymer, a high butylene content S-$EB_n$-S block copolymer, and a high polyisopropylethyene content S-$EP_n$-S block copolymer vi) S-E-EB$_{>70}$-E-S gels made by coupling S-E-EB$_{>70}$.

vii) S-E-EP$_{>70}$-E-S gels made by coupling S-E-EP$_{>70}$.

viii) gels made from linear, branched, radial, star-shaped, multi-arm or branched block copolymers having sufficient multiple midblock components of high crystalline ethylene content, high butylene content, and/or high isopropylethyene content including all combinations and permutations and mixtures of such block copolymers and as further described below.

Generally, one or more (E) midblocks can be incorporated at various positions along the midblocks of the block copolymer's. Using the sequential process for block copolymer synthesis, The (E) midblocks can be positioned as follows:

i) A-E-W-A
ii) A-E-W-E-A
iii) A-W-E-W-A
iv) and etc.

The highly amorphous or highly crystalline midblock components:

v) A-W-A
vi) A-E-A

The lower flexibility of block copolymer crystal gels due to (E) midblocks can be balanced by the addition of sequentially (W) midblocks. For example, the sequentially synthesized block copolymer S-E-EB-S can maintain a high degree of flexibility due to the presence of amorphous -EB- block. The sequential block copolymer S-E-EB-B-S can maintain a high degree of flexibility due to the presence of amorphous -EB- and -B- midblocks. The sequential block copolymer S-E-EP-E-S can maintain a high degree of flexibility due to the presence of -EP- midblock. The sequential block copolymer S-E-B-S can maintain a high degree of flexibility due to the presence of the -B-, butylene midblock. For S-E-S, where the midblock is substantially crystalline and flexibility low, physical blending with amorphous block copolymers such as S-EB-S, S-B-S, S-EP-S, S-EB-EP-S, (S-EP)$_n$ and the like can produce more softer, less rigid, and more flexible crystal gel.

In additional to the block copolymers S-E-EB-S and S-E-EP-S, S-E-EB-E-S can be made by coupling S-E-EB and S-E-EP-E-S can be made by coupling S-E-EP or by making it sequentially. Multi-arm of such block copolymer can also be made.

Because of the (E) midblocks, the crystal gels forming the floss of the invention exhibit different physical characteristics and improvements over substantially amorphous gels including damage tolerance, improved crack propagation resistance, improved tear resistance producing knotty tears as opposed to smooth tears, crystalline melting point of at least 28° C., improved resistance to fatigue, higher hysteresis, etc. Moreover, the crystal gels forming the floss when stretched exhibit additional yielding as shown by necking caused by stress induced crystallinity.

Regarding resistance to fatigue, fatigue (as used herein) is the decay of mechanical properties after repeated application of stress and strain. Fatigue tests give information about the ability of a material to resist the development of cracks or crazes resulting from a large number of deformation cycles. Fatigue test can be conducted by subjecting samples of amorphous and crystal gels to deformation cycles to failure (appearance of cracks, crazes, rips or tears in the gels).

Tensile strength can be determined by extending a selected gel sample to break as measured at 180° U bend around a 5.0 mm mandrel attached to a spring scale. Likewise, tear strength of a notched sample can be determined by propagating a tear as measured at 180° U bend around a 5.0 mm diameter mandrel attached to a spring scale.

Various block copolymers can be obtained which are amorphous, highly rubbery, and exhibiting minimum dynamic hysteresis:

Block copolymer S-EB-S

The monomer butadiene can be polymerized in a ether/hydrocarbon solvent to give a 50/50 ratio of 1,2 poly (butadiene)/1,4 poly(butadiene) and on hydrogenation no long runs of —CH$_2$— groups and negligible crystallinity, ie, about $(0.5)^4$ or 0.06 or 6% and actual crystallinity of about 3%. Due to the constraints of T$_g$ and minimum hysteresis, conventional S-EB-S have ethylene-butylene ratios of about 60:40 with a crystallinity of about $(0.6)^4$ or 0.129 or 12% and actual crystallinity of about 7.7%.

Block copolymer S-EP-S

The monomer isoprene when polymerized will produce 95% 1,4 poly(isoprene)/5% 3,4 polycisoprene) and upon hydrogenation will form amorphous, rubbery poly(ethylene-propylene) midblock and no long runs of —CH$_2$— and no crystallinity.

Mixed block copolymer S-EB/EP-S

The polymerization of a 50/50 mixture of isoprene/butadiene monomers in suitable ether/hydrocarbon solvents to give equal amounts of 1,2 and 1,4 poly(butadiene) on hydrogenation will produce a maximum crystallinity of $(0.25)^4$ or 0.4%. The actual crystallinity would be approximately about 0.2%, which is negligible and results in a good rubbery midblock.

The polymerization of a 80/20 mixture of isoprene/butadiene monomers in suitable ether/hydrocarbon solvents to give equal amounts of 1,2 and 1,4 poly(butadiene) will upon hydrogenation produce a low crystallinity of $(0.10)^4$ or 0.01%. The actual crystallinity would be approximately about 0.006%, which is negligible and results in a good rubbery midblock.

The polymerization of a 20/80 mixture of isoprene/butadiene monomers in suitable ether/hydrocarbon solvents to give equal amounts of 1,2 and 1,4 poly(butadiene) will upon hydrogenation produce a low crystallinity of $(0.4)^4$ or 2.56%. The actual crystallinity would be approximately about 1.53%, which is negligible and results in a good rubbery midblock.

The polymerization of a 20/80 mixture of isoprene/butadiene monomers in suitable ether/hydrocarbon solvents to give a 40:60 ratio of 1,2 and 1,4 poly(butadiene) will upon hydrogenation produce a low crystallinity of $(0.48)^4$ or 5.3%. The actual crystallinity would be approximately about 3.2%, which is negligible and results in a good rubbery midblock.

The midblocks (Z) of one or more -E-, -B-, -EB-, or -EP- can comprise various combinations of midblocks between the selected end blocks (A); these include: -E-EB-, -E-EP-, -B-EP-, -B-EB-, -E-EP-E-, -E-EB-B-, -B-EP-B-, -B-EB-B-, -E-B-EB-, -E-B-EP-, -EB-EP-, -E-EB-EP-, -E-EP-EB-, -B-EB-EP-, -B-EP-EB-, -E-EP-E-EP-, -E-EP-E-EB-, -B-EP-B-EP-, -B-EB-B-EB-, -B-EB-B-EP-, -E-EB-B-EP-, -E-EP-B-EB- and the like.

The block copolymers of (A-Z-A) can be obtained by sequential synthesis methods followed by hydrogenation of the midblocks. As denoted above, abbreviations are interchangeably used, for example, (S-E-EP-S) denotes poly (styrene-ethylene-ethylene-co-propylene-styrene). Other linear block copolymers (denoted in abbreviations) include the following: (S-E-S), (S-E-EB-S), (S-E-EP-S), (S-B-EP-S), (S-B-EB-S), (S-E-EP-E-S), (S-E-EB-B-S), (S-B-EP-B-S), (S-B-EB-B-S), (S-E-B-EB-S), (S-E-B-EP-S), (S-EB-EP-S), (S-E-EB-EP-S), (S-E-EP-EB-S), (S-B-EB-EP-S), (S-B-EP-EB-S) and the like.

The multiblock star-shaped (or radial) copolymers $(A-Z)_n X$ can be obtained by sequential synthesis methods including hydrogenation of selected block copolymers made by polymerizing half of the block copolymers such as SBS or SIS and couple the halves with a coupling agent such as an organic dihalide; or couple with an agent such as SnC14, which results in star-shaped block copolymers (four branches). Coupling with divinyl benzene give block copolymers which are very highly branched. Radial block copolymers suitable for use in forming the crystal gels of the present invention include: $(S-E)_n$, $(S-E-EB)_n$, $(S-E-EP)_n$, $(S-B-EP)_n$, $(S-B-EB)_n$ $(S-E-EP-E)_n$, $(S-E-EB-B)_n$, $(S-B-EP-B)_n$, $(S-B-EB-B)_n$, $(S-E-B-EB)_n$, $(S-E-B-EP)_n$, $(S-EB-EP)_n$, $(S-E-EB-EP)_n$, $(S-E-EP-EB)_n$, $(S-B-EB-EP)_n$, $(S-B-EP-EB)_n$, $(S-E-EP-EP)_n$, $(S-E-EP-EB)_n$, $(S-EP-B-EP)_n$, $(S-B-EB-B-EB)_n$, $(S-B-EB-B-EP)_n$, $(S-E-EB-B-EP)_n$ and counter part multifunctional block copolymers:$(R)_n$-E-S, $(R)_n$-E-EB-S, $(R)_n$-E-EP-S, $(R)_n$-E-EP-E-S, $(R)_n$-E-EB-B-S, $(R)_n$-E-B-EB-S, $(R)_n$-E-B-EP-S, $(R)_n$-E-EB-EP-S, $(R)_n$-E-EP-EB-S and the like. In the above notation, "-E-" denotes substantially crystalline polyethylene midblock.

The selected amount of crystallinity in the midblock should be sufficient to achieve improvements in one or more physical properties including improved damage tolerance, improved crack propagation resistance, improved tear resistance, improved resistance to fatigue of the bulk gel and resistance to catastrophic fatigue failure of crystal gel composites, such as between the surfaces of the crystal gel and substrate or at the interfaces of the interlocking materials) and crystal gel, which improvements are not found in amorphous gels at corresponding gel rigidities.

Selected (I) linear, branched, radial, star-shaped, multi-arm or branched block copolymers utilized in forming the crystal gels forming the floss of the invention are characterized as having an ethylene to butylene midblock ratio (E:B) of about 85:15 to about 65:35. Advantageously, the butylene concentration of the midblock is about 35% or less, more advantageously, about 30% or less, still more advantageously, about 25% or less, especially advantageously, about 20% or less. Advantageously, the ethylene to butylene midblock ratios can range from about 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, 70:30, 69:31, 68:32, 67:33, 66:34 to about 65:35.

The A to Z midblock ratio of the block copolymers suitable for forming crystal gels of the invention can range from about 20:80 to 40:60 and higher. More specifically, the values can be 15:85, 19:81, 20:80, 21:79. 22:78. 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 51:49 and 52:48.

The crystal gels forming the floss can optionally comprise selected major or minor amounts of one or more polymers or copolymers (II) provided the amounts and combinations are selected without substantially decreasing the desired properties. The polymers and copolymers can be linear, star-shaped, radial, branched, or multiarm; these including: (SBS) styrene-butadiene-styrene block copolymers, (SIS) styrene-isoprene-styrene block copolymers, low and medium viscosity (S-EB-S) styrene-ethylene-butylene-styrene block copolymers, (S-EP) styrene-ethylene-propylene block copolymers, (S-EP-S) styrene-ethylene/propylene-styrene block copolymers, (S-EP-S-EP) styrene-ethylene/propylene-styrene-ethylene/propylene) block copolymers, (S-E-EPS) styrene-ethylene-ethylene/propylene-styrene block copolymers, $(SB)_n$ styrene-butadiene and $(S-EB)_n$, $(S-EB-S)_n$, $(S-E-EP)_n$ $(SEP)_n$, $(SI)_n$ multi-arm, radial, branched or star-shaped copolymers, polyethyleneoxide (EO), poly(dimethylphenylene oxide), teflon (TFE, PTFE, PEA, FEP, etc), optical clear amorphous copolymers based on 2,2-bistrifluoromethyl-4,5-difuoro-1, 3-dioxole (PDD) and tetrafluoroethylene (TFE), maleated S-EB-S block copolymer, polycarbonate, ethylene vinyl alcohol copolymer, and the like. Still, other (II) polymers include homopolymers which can be utilized in minor amounts; these include: polystyrene, polydimethylsiloxane, polyolefins such as polybutylene, polyethylene, polyethylene copolymers, polypropylene, and the like. Polyurethane elastomers based on saturated hydrocarbon diols (Handlin, D., Chin. S., and Masse. M., et al. "POLYURETHANE ELASTOMERS BASED ON NEW SATURATED HYDROCARBON DIOLS" Published Society of Plastics Industry, Polyurethane Division, Las Vegas, Oct. 23, 1996) are also suitable for use in blending with the block copolymers (I) used in forming the crystal gels of the invention. Such saturated hydrocarbon diols include hydroxyl terminated oligomers of poly(ethylene-butylene) (EB), poly (ethylene-propylene) (EP), -E-EB-, -E-EP-, -B-EP-, -B-EB-, -E-EP-E-, -E-EB-B-, -B-EP-B-, -B-EB-B-, -E-B-EB-, -E-B-EP-, -EB-EP-, -E-EB-EP-, -E-EP-EB-, -B-EB-EP-, -B-EP-EB-, -E-EP-E-EP-, -E-EP-E-EB-, -B-EP-B-EP-, -B-EB-B-EB-, -B-EB-B-EP-, -E-EB-B-EP-, -E-EP-B-EB- and the like. As an example, thermoplastic polyurethane made with isocyanates and chain extenders such as TMPD and BEPD from saturated hydrocarbon diol KLP L-2203 having a hard segment contents of 22% exhibits clean phase separation of the hard and soft segments with glass a transition of –50° C. KLP L-2203 based TPU's can be mixed with the crystalline block copolymers to form soft crystal gels within the gel rigidity ranges of the invention. High butylene content SEBS block copolymers include Shell high molecular weight GRP6917 having a rubber Tg of about –38° C. to about –22° C., preferably –27° C., Toluene Viscosity at 10% solids at 25° C. of about 40 cp to about 120 cp, preferably about 70 cp and styrene content of about 20 to about 40, preferably about 33, tensile strength, psi of about 4000, elongation at break of about 600%.

Suitable polyolefins include polyethylene and polyethylene copolymers such as Dow Chemical Company's Dowlex 3010, 2021D, 2038, 2042A, 2049, 2049A, 2071, 2077, 2244A, 2267A; Dow Affinity ethylene alpha-olefin resin PL-1840, SE-1400, SM-1300; more suitably: Dow Elite 5100, 5110, 5200, 5400, Primacor 141--XT, 1430, 1420, 1320, 3330, 3150, 2912, 3340, 3460; Dow Attane (ultra low density ethylene-octene-1 copolymers) 4803, 4801, 4602,

The conventional term "major" means about 51 weight percent and higher (e.g. 55%, 60%, 65%, 70%, 75%, 80% and the like) and the term "minor" means 49 weight percent and lower (e.g. 2%, 5%, 10%, 15%, 20%, 25% and the like).

Example of (II) polymers, copolymers, and blends include: (a) Kraton G 1651, G 1654X; (b) Kraton G 4600; (c) Kraton G 4609; other suitable high viscosity polymer and oils include: (d) Tuftec H 1051; (e) Tuftec H 1041; (f) Tuftec H 1052; (g) Kuraray SEPS 4033; (h) Kuraray S-EB-S 8006; (i) Kuraray SEPS 2005; (j) Kuraray SEPS 2006, and (k) blends (polyblends) of (a)–(h) with other polymers and copolymers include: (1) S-EB-S/SBS; (2) S-EB-S/SIS; (3) S-EB-S/(SEP); (4) S-EB-S/(SEB)$_n$; (5) S-EB-S/(SEB)$_n$; (6) S-EB-S/(SEP)$_n$; (7) S-EB-S/(SI)n; (8) S-EB-S/(SI) multi-arm; (9) S-EB-S/(SEB)$_n$; (10) (SEB)$_n$ star-shaped copolymer; (11) s made from blends of (a)–(k) with other homopolymers include: (12) S-EB-S/polystyrene; (13) S-EB-S/polybutylene; (14) S-EB-S/polyethylene; (14) S-EB-S/polypropylene; (16) SEP/S-EB-S, (17) SEP/SEPS, (18) SEP/SEPS/SEB, (19), SEPS/S-EB-S/SEP, (20), SEB/S-EB-S (21), EB-EP/S-EB-S (22), S-EB-S/EB (23), S-EB-S/EP (24), (25) (SEB)$_n$ s, (26) (SEP)$_n$, (27) Kuraray 2007 (SEPS), (28) Kuraray 2002, (SEPS), (29) Kuraray 4055 (S-EB-EP-S) (30) Kuraray 4077 (S-EB-EP-S) (31) Kuraray 4045 (S-EB-EP-S) (32) (S-EB-EP)$_n$, (33) (SEB)$_n$, (34) EPDM, (35) EPR, (36) EVA, (37) coPP, (38) EMA, (39) EEA, (40) DuPont Teflon AF amorphous fluoropolymers, (41) Dow polydimethylsiloxane, (42) maleated S-EB-S (maleation level 2–30%), (43) (EP)$_n$, (44) Kraton GRP6918 and the like.

Representative examples of commercial elastomers that can be combined with the block copolymers (I) described above include: Shell Kratons D1101, D1102, D1107, D1111, D1112, D1113X, D1114X, D1116, D1117, D1118X, D1122X, D1125X, D1133X, D1135X, D1184, D1188X, D1300X, D1320X, D4122, D4141, D4158, D4240, G1650, G1652, G1657, G1701X, G1702X, G1726X, G1750X, G1765X, FG1901X, FG1921X, D2103, D2109, D2122X, D3202, D3204, 33226, D5298, D5999X, D7340, G1650, G1651, G1652, G4609, G4600, G1654X, G2701, G2703, G2705, G1706, G2721X, G7155, G7430, G7450, G7523X, G7528X, G7680, G7705, G7702X, G7720, G7722X, G7820, G7821X, G7827, G7890X, G7940, G1730M, FG1901X and FG1921X. Kuraray's SEP, SEPS, S-EB-S, S-EB-EP-S Nos. 1001, 1050, 2027, 2003, 2006, 2007, 2008, 2023, 2043, 2063, 2050, 2103, 2104, 2105, 4033, 4045, 4055, 4077, 8004, 8006, 8007 and the like.

The amorphous S-EB-S and (S-EB)n (II) copolymers can have a broad range of styrene to ethylene-butylene ratios (S:EB) of about 20:80 or less to about 40:60 or higher. The S:EB weight ratios can range from lower than about 20:80 to above about 40:60 and higher.

The Brookfield Viscosity of a 5 weight percent solids solution in toluene at 30° C. of 2006, 4045, 4055, 4077 typically range about 20–35, about 25–150, about 60–150, about 200–400 respectively. Typical Brookfield Viscosities of a 10 weight percent solids solution in toluene at 30° C. of 1001, 1050, 2007, 2063, 2043, 4033, 2005, 2006, are about 70, 70, 17, 29, 32, 50, 1200, and 1220 respectively. Typical Brookfield Viscosity of a 25 weight percent solids solution in toluene at 25° C. of Kraton D1101, D1116, D1184, D1300X, G1701X, G1702X are about 4000, 9000, 20000, 6000, 50000 and 50000 cps respectively. Typical Brookfield Viscosity of a 10 weight percent solids solution in toluene at 25° C. of G1654X is about 370 cps.

Suitable block copolymers (II) and their typical viscosities are further described. Shell Technical Bulletin SC:1393-92 gives solution viscosity as measured with a Brookfield model RVT viscometer at 25° C. for Kraton G 1654X at 10% weight in toluene of approximately 400 cps and at 15% weight in toluene of approximately 5,600 cps. Shell publication SC:68–79 gives solution viscosity at 25° C. for Kraton G 1651 at 20 weight percent in toluene of approximately 2,000 cps. When measured at 5 weight percent solution in toluene at 30° C., the solution viscosity of Kraton G 1651 is about 40. Examples of high viscosity S-EB-S triblock copolymers includes Kuraray's S-EB-S 8006 which exhibits a solution viscosity at 5 weight percent at 30° C. of about 51 cps. Kuraray's 2006 SEPS polymer exhibits a viscosity at 20 weight percent solution in toluene at 30° C. of about 78,000 cps, at 5 weight percent of about 27 cps, at 10 weight percent of about 1220 cps, and at 20 weight percent 78,000 cps. Kuraray SEPS 2005 polymer exhibits a viscosity at 0.5 weight percent solution in toluene at 30° C. of about 28 cps, at 10 weight percent of about 1200 cps, and at 20 weight percent 76,000 cps. Other grades of S-EB-S, SEPS, (SEB)$_n$ (SEP)$_n$ polymers can also be utilized in the present invention provided such polymers exhibits the required high viscosity. Such S-EB-S polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C..

The styrene to ethylene and butylene (S:EB) weight ratios for the Shell designated polymers can have a low range of 20:80 or less. Although the typical ratio values for Kraton G 1651, 4600, and 4609 are approximately about 33:67 and for Kraton G 1855X approximately about 27:73, Kraton G 1654X (a lower molecular weight version of Kraton G 1651 with somewhat lower physical properties such as lower solution and melt viscosity) is approximately about 31:69, these ratios can vary broadly from the typical product specification values. In the case of Kuraray's S-EB-S polymer 8006 the S:EB weight ratio is about 35:65. In the case of Kuraray's 2005 (SEPS), and 2006 (SEPS), the S:EP weight ratios are 20:80 and 35:65 respectively. The styrene to ethylene-ethylene/propylene (S:EB-EP) ratios of Kuraray's SEPTON 4045, 4055, and 4077 are typically about 37.6, 30, 30 respectively. More typically the (S:EB-EP) and (S:EP) ratios can vary broadly much like S:EB ratios of S-EB-S and (SEB)$_n$ from less than 19:81 to higher than 51:49 (as recited above) are possible. It should be noted that multiblock copolymers including SEPTON 4045, 4055, 4077 and the like are described in my cited copending parent applications and are the subject matter of related inventions.

The block copolymers (II) such as Kraton G 1654X having ratios of 31:69 or higher can be used and do exhibit about the same physical properties in many respects to Kraton G 1651 while Kraton G 1654X with ratios below 31:69 may also be use, but they are less advantageous due to their decrease in the desirable properties of the final gel.

Plasticizers (III) particularly advantageous for use in practicing the present invention are will known in the art, they include rubber processing oils such as paraffinic and naphthenic petroleum oils, highly refined aromatic-free paraffinic and naphthenic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight.

The amount of plasticizing oil (III) sufficient to achieve gel rigidities of from less than about 2 gram Bloom to about 1,800 gram Bloom range from less than about 250 to about 3,000 parts by weight of a plasticizing oil.

Examples of representative commercially available plasticizing oils include Amoco® polybutenes, hydrogenated polybutenes, polybutenes with epoxide functionality at one end of the polybutene polymer, liquid poly(ethylene/butylene), liquid hetero-telechelic polymers of poly (ethylene/butylene/styrene) with epoxidized polyisoprene and poly(ethylene/butylene) with epoxidized polyisoprene: Example of such polybutenes include: L-14 (320 Mn), L-50 (420 Mn), L-100 (460 Mn), H-15 (560 Mn), H-25 (610 Mn), H-35 (660 Mn), H-SO (750 Mn), H-100 (920 Mn), H-300 (1290 Mn), L-14E (27–37 cst @100° F. Viscosity), H-300E (635–690 cst @210° F. Viscosity), Actipol E6 (365 Mn), E16 (973 Mn), E23 (1433 Mn), Kraton L-2203 and Kraton L-1203, EKP-206, EKP-207, HPVM-2203 and the like. Example of various commercially oils include: ARCO Prime (55, 70, 90, 200, 350, 400 and the like), Duraprime and Tufflo oils (6006, 6016, 6016M, 6026, 6036, 6056, 6206, etc) , other white mineral oils include: Bayol, Bernol, American, Blandol, Drakeol, Ervol, Gloria, Kaydol, Litetek, Lyondell (Duraprime 55, 70, 90, 200, 350, 400, etc), Marcol, Parol, Peneteck, Primol, Protol, Sontex, Witco brand white oils including RR-654-P and the like. Generally, plasticizing oils with average molecular weights less than about 200 and greater than about 700 may also be used (e.g., H-300 (1290 Mn)).

Comparisons of oil extended S-EB-S triblock copolymers have been described in Shell Chemical Company Technical Bulletin SC:1102-89 (April 1989) "KRATON® THERMOPLASTIC RUBBERS IN OIL GELS" which is incorporated herein by reference.

The crystal gels forming the floss can be made non-adhearing, non-sticking, (non-tacky), by incorporating an advantage amount of stearic acid (octadecanoic acid), metal stearates (e.g., calcium stearate, magnesium stearate, zinc stearate, etc.), polyethylene glycol distearate, polypropylene glycol ester or fatty acid, and polytetramethylene oxide glycol disterate, waxes, stearic acid and waxes, metal stearate and waxes, metal stearate and stearic acid. The use of stearic acid alone do not reduce tack. The amount of stearic acid is also important. As an example, ratio of 200 grams stearic acid to 2,000 gram of S-EB-S (a ratio of 0.1) will result in spotted tack reduction on the surface of the gel. A ratio of 250 to 2,000 will result in spotted crystallized stearic acid regions on the surface of the gel or spotted tack reduction. A ratio of 300 to 2,000 will result in complete tack reduction with large stearic acid crystallized regions on the surface of the gel. When microcrystalline waxes are incorporated together with stearic acid, the crystallization of stearic acid completely disappears from the surface of the gel. For example excellent result is achieved with 200 grams of stearic acid, 150 grams of microcrystalline wax and 2,000 grams of S-EB-S. The same excellent result is achieved when S-EB-S is adjusted to 3,000 grams, 4,000 grams, etc. The same result is achieved with (I) copolymers as well as in combination with polymers (II) such as SEPS, S-EB-EP-S, (S-EB-EP)$_n$, (SEB)$_n$, (SEP)$_n$ polymers. Moreover, when about 50 grams of tetrakistmethylene 3-(3'5'di-tertbutyl-4"-hydroxyphenyl) propionate) methane is use as a tack reducing blooming agent, tack is completely removed from the surface of the gel after two to three weeks of blooming.

The crystal gels forming the floss can also contain useful amounts of conventionally employed additives such as stabilizers, antioxidants, antiblocking agents, colorants, fragrances, flame retardants, flavors, other polymers in minor amounts and the like to an extend not affecting or substantially decreasing the desired properties. Additives useful in the crystal gel of the present invention include: tetrakis(methylene 3-(3',5'-di-tert-butyl-4"-hydroxyphenyl) propionate) methane, octadecyl 3-(3",5"-di-tertbutyl-4"-hydroxyphenyl) propionate, distearyl-pentaerythritol-diproprionate, thiodiethylene bis-(3,5-ter-butyl-4-hydroxy) hydrocinnamate, (1,3,5-trimethyl-2,4,6-tris[3,5-di-tert-butyl-4-hydroxybenzyl] benzene), 4,4"-methylenebis(2,6-di-tert-butylphenol), steraric acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, calcium sterate, other metal sterates, waxes (e.g., polyethylene, polypropylene, microcrystalline, carnauba, paraffin, montan, candelilla, beeswax, ozokerite, ceresine, and the like), teflon (TFE, PTFE, PEA, FEP, etc), polysiloxane, etc. The crystal gel can also contain metallic pigments (aluminum and brass flakes), TiO2, mica, fluorescent dyes and pigments, phosphorescent pigments, aluminatrihydrate, antimony oxide, iron oxides ($Fe_3O_4$, —$Fe_2O_3$, etc.), iron cobalt oxides, chromium dioxide, iron, barium ferrite, strontium ferrite and other magnetic particle materials, molybdenum, silicones, silicone fluids, lake pigments, aluminates, ceramic pigments, ironblues, ultramarines, phthalocynines, azo pigments, carbon blacks, silicon dioxide, silica, clay, feldspar, glass microspheres, polymer microspheres, barium ferrite, wollastonite and the like. The report of the committee on Magnetic Materials, Publication NMAB-426, National Academy Press (1985) is incorporated herein by reference.

The crystal gels denoted as "G" can be physically interlocked with a selected material denoted as "M" to form composites as denoted for simplicity by their combinations $G_nM_n$, $G_nM_nG_n$1 $M_nG_nM_n$, $M_nG_nG_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nM_nM_nG_n$, $G_nG_nM_nM_n$, $G_nG_nM_nG_nM_n$, $G_nM_nG_nG_n$, $G_nG_nM_n$, $G_nM_nG_nM_nM_n$, $M_nG_nM_n$ $G_nM_nG_n$, $G_nG_nM_nM_nG_n$, $G_nG_nM_nG_nM_n$ $G_n$, and the like or any of their permutations of one or more $G_n$ with $M_n$ and the like, wherein when n is a subscript of M, n is the same or different selected from the group consisting of foam, plastic, fabric, metal, concrete, wood, glass, ceramics, synthetic resin, synthetic fibers or refractory materials and the like; wherein when n is a subscript of G, n denotes the same or a different gel rigidity of from about 2 gram to about 1,800 gram Bloom). The gels of the composites can be formed in combination with a selected amount of at least one polymer or copolymer selected from the group consisting of poly (styrene-butadiene-styrene), poly(styrene-butadiene), poly (styrene-isoprene-styrene), poly(styrene-isoprene), poly (styrene-ethylene-propylene), low viscosity poly(styrene-ethylene-propylene-styrene), low viscosity poly(styrene-ethylene-butylene-styrene), poly(styrene-ethylene-butylene), polystyrene, polybutylene, poly(ethylene-propylene), poly(ethylene-butylene), polyproplyene, or polyethylene, wherein said selected copolymer is a linear, branched, multiarm, or star shaped copolymer are useful as dental floss.

The crystal gels forming the floss are prepared by blending together the components including other additatives as desired at about 23° C. to about 100° C. forming a paste like mixture and further heating said mixture uniformly to about 150° C. to about 200° C. until a homogeneous molten blend is obtained. Lower and higher temperatures can also be utilized depending on the viscosity of the oils and amounts of multiblock copolymers (I) and polymer (II) used. These components blend easily in the melt and a heated vessel equipped with a stirrer is all that is required. Small batches can be easily blended in a test tube using a glass stirring rod for mixing. While conventional large vessels with pressure and/or vacuum means can be utilized in forming large batches of the instant crystal gels in amounts of about 40 lbs or less to 10,000 lbs or more. For example, in a large vessel, inert gases can be employed for removing the composition from a closed vessel at the end of mixing and a partial vacuum can be applied to remove any entrapped bubbles. Stirring rates utilized for large batches can range from about less than 10 rpm to about 40 rpm or higher.

The crystal gel articles can be formed by blending, injection molding, extruding, spinning, casting, dipping and other conventional methods. For example, Shapes having various cross-section can be extruded. The crystal gels can also be formed directly into articles or remelted in any suitable hot melt applicator and extruded into shaped articles and films or spun into threads, strips, bands, yarns, or other shapes. With respect to various shapes and yarn, its size are conventionally measured in denier (grams/9000 meter), tex (grams/1000 meter), and gage (1/2.54 cm). Gage, tex, denier can be converted as follows: tex=denier/9=specific gravity (2135/gage), for rectangular cross section, tex=specific gravity (5806×103) (th) (w)/9, where th is the thickness and w the width of the strip, both in centimeters. General descriptions of (1) block copolymers, (2) elastomeric fibers and conventional (3) gels are found in volume 2, starting at pp. 324–415, volume 6, pp 733–755, and volume 7, pp. 515 of ENCYCLOPEDIA OF POLYMER SCIENCE AND ENGINEERING, 1987 which volumes are incorporated herein by reference.

Not only do the crystal gels forming the floss have all the desirable combination of physical and mechanical properties substantially similar to high viscosity amorphous S-EB-S gels such as high elongation at break of at least 1,600%, ultimate tensile strength of about $8 \times 10^5$ dyne/cm$^2$ and higher, low elongation set at break of substantially not greater than about 2%, substantially about 100% snap back when extended to 1,200% elongation, and a gel rigidity of substantially from about 2 gram to about 1,800 gram Bloom and higher, the crystal gels of the present invention exhibit improved tear resistance and resistance to fatigue not obtainable from amorphous S-EB-S or S-EP-S gels at corresponding gel rigidities.

The crystal gels forming the floss of the present invention exhibit one or more of the following properties. These are: (1) tensile strength of about $8 \times 10^5$ dyne/cm$^2$ to about $10^7$ dyne/cm$^2$ and greater; (2) elongation of less than about 1,600% to about 3,000% and higher; (3) elasticity modules of about $10^4$ dyne/cm$^2$ to about $10^6$ dyne/cm$^2$ and greater; (4) shear modules of about $10^4$ dyne/cm$^2$ to about $10^6$ dyne/cm$^2$ and greater as measured with a 1, 2, and 3 kilogram load at 23° C.; (5) gel rigidity of about less than about 2 gram Bloom to about 1,800 gram Bloom and higher as measured by the gram weight required to depress a gel a distance of 4 mm with a piston having a cross-sectional area of 1 square cm at 23° C.; (6) tear propagation resistance greater than the tear resistance of amorphous S-EB-S gels at corresponding gel rigidities; (7) resistance to fatigue greater than the fatigue resistance of amorphous S-EB-S gels at corresponding gel rigidities; (8) and substantially 100% snap back recovery when extended at a crosshead separation speed of 25 cm/minute to 1,200% at 23° C. Properties (1), (2), (3), and (6) above are measured at a crosshead separation speed of 25 cm/minute at 23° C.

The crystal gels can be formed in any shape; the original shape can be deformed into another shape (to contact a regular or regular surface) by pressure and upon removal of the applied pressure, the composition in the deformed shape will recover back to its original shape.

For purposes of dental flossing, while flossing between two closely adjacent teeth, especially between two adjacent teeth with substantial contact points and more especially between two adjacent teeth with substantial amalgam alloy metal contact points showing no gap between the teeth, it is critical that the crystal gel resist tearing, shearing, and crazing while being stretched to a high degree in such situations. For example, dental crystal gel floss can take the form of a disk where the segments of the circumference of the disk is stretched for flossing between the teeth. Other shaped articles suitable for flossing include threads, strips, yarns, tapes, etc., mentioned above.

In all cases, the tear strength of crystal gels are higher than that of amorphous gels. For example, the crystal gels made from high viscosity S-E-EB-S and S-E-EP-S copolymers are resistant to tearing when under high stress or shear than high viscosity typical S-EB-S and S-EP-S copolymer gels.

In order for gels to be useful as a dental floss, it must overcome the difficult barriers of high shearing and high tearing under extreme elongation and tension loads. The difficulties that the gels must overcome during flossing can be viewed as follows: during the action of flossing, the gel is stretched from no less than about 200% to about 1,100% or higher, the gel floss is deformed as it is pulled down with tearing action between the contacting surfaces of the teeth, then, the wedge of gel floss is sheared between the inner contacting surfaces of the teeth, and finally, the elongated wedged of gel floss is pulled upwards and out between the surfaces of the teeth. The forces encountered in the act of flossing are: tension, shearing, tearing under extreme tension.

This invention advances the flossing art by providing strong, soft, and extreme tear resistant gels made from multiblock copolymers which gels are substantially as soft as the gums surrounding the teeth.

Gel floss formed from the gels has many advantages over conventional dental floss such as regular and extra fine waxed and unwaxed nylon floss, spongy nylon fiber floss, and waxed and unwaxed expanded and unexpended teflon floss. Such conventional floss are not recommended for use by children, since a slip or sudden snap in forcing the floss between the teeth may cause injury to the gums which often times results in bleeding. For sensitive gums and inflamed gums which has become red and puffy, it is difficult to floss at, near, and below the gumline. The soft gel floss with softness substantially matching the softness of the gums are of great advantage for use by children and for flossing teeth surrounded by sensitive and tender gums.

The shear resistant characteristics of the gels can be indirectly determined by subjecting the gel to the shear forces of a pair of twisting strings and the resulting inward pulling forces of the twisting strings can be directly read off of a spring scale. As a pair of strings are gradually twisted, typical values will range from less than one pound to fifty pounds and greater. As the string is being twisted (simulating increased shearing forces), the measured pulling forces can range from a low value of 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 . . . to values of 40, 50, 60, 70, 80 pounds and greater.

Gel material of low strength can not resist the tremendous shearing action of the twisting strings. The twisting action of the strings can exhibit a first order twist, a second order twist, or higher order twists. A first order twist refers to one or more twists of a pair of strings (i.e., a pair of strings when twisted together forms a small tight binding helix). A second order twist refers to one or more large binding helixes build up by a pair of strings that have been twisted beyond the maximum number of twist which normally produce small tight binding helixes of the first order kind. Similarly, a third order twist refers to a much larger tightly binding helix build up by the maximum number of second order twists produced by the pair of twisting strings. The third order twist may be manifested by the appearance of a branch of two or more twist of the first order twisting strings.

The order of twisting will increase (from a one, two, three, and higher order twist) until the rubber band breaks. Likewise, a looped string with one end attached to a spring scale and the other end attached to a fixed anchor can be twisted into a first, second, third, and higher ordered twist state. This method can be utilized to directly measure the force generated for each ordered twist states. The static force generated by twisting a string on a spring scale is a way of determining the shear force generated in the shearing action of forcing the gel floss between two closely contacting teeth when flossing.

In considering dental flossing criteria, one or more of the following conditions can be regarded as critical factors for dental flossing gels.

SHEAR RESISTANT CRITERIA

For the gels to be considered useful for flossing, the gels, critically, should withstand a twisting string shearing force of at least about 5 Kg, more advantageously at least about 8 Kg, and still more advantageously at least about 10 Kg of inward pulling force of a pair of twisting strings measured directly on a spring scale.

FLOSSING CYCLE CRITERIA

For the gels to be considered useful for flossing, the gels, critically, should advantageously be able to perform at least 4 flossing cycles, more advantageously 8 cycles, and still more advantageously of about 20 cycles without breaking apart when a 3.0 mm diameter gel strand is tested on a set of simulated upper front teeth fully contacting under a uniform spring load of (0.9027 Kg) two pounds. The simulated upper front teeth comprises two small stainless steel rollers (3/8" dia.) facing lengthwise parallel and forced together so as to form a contact length of ½ inches under a spring load of two pounds as measured by a Entran® model ELO-200-4 load cell adjusted by a straight micrometer at room temperature.

GEL STRENGTH CRITERIA

For the gels to be considered useful for flossing, the gels, critically, should advantageously exhibit a tensile strength of at least 5 Kg/cm$^2$ (when extended to break as measured at 180° U bend around a 5.0 mm mandrel attached to a spring scale) and more advantageously at least 8 Kg/cm$^2$, and still more advantageously of about 10 Kg/cm$^2$ and higher. The high and gels useful as dental floss can exhibit tensile strengths at break of at least 20 Kg/cm$^2$, more advantageously of at least 40 Kg/cm$^2$, and exceptionally more advantageously at least 60 Kg/cm$^2$. Typically, the tensile strengths range from about 20 Kg/cm$^2$ to about 110 Kg/cm2 and higher, more typically from about 30 Kg/cm$^2$ to 80 Kg/cm$^2$ and higher, especially more typically from about 40 Kg/cm$^2$ to about 90 Kg/cm$^2$ and higher, and exceptionally typically from about 50 Kg/cm$^2$ to about 100 Kg/cm$^2$ and higher.

PROPAGATING TEAR CRITERIA

As a minimum, for the Gels to be considered useful for flossing, the gels, critically, should advantageously exhibit a propagating tear force (when propagating a tear as measured at 180° U bend around a 5.0 mm diameter mandrel attached to a spring scale) of at least about 1 Kg/cm, more advantageously at least 2 Kg/cm, and still more advantageously of about 3 Kg/cm and higher. The gels useful as dental floss can exhibit tear strengths of at least 4 Kg/cm and higher, more advantageously of at least 6 Kg/cm and higher, exceptionally more advantageously of at least 8 Kg/cm and higher. Typically, the tear propagation strength can range from about 5 Kg/cm to about 20 Kg/cm and higher, more typically from about less than 5 Kg/cm to about 25 Kg/cm and higher, especially more typically form about less than 6 Kg/cm to about 30 Kg/cm and higher, and exceptionally more typically from about less than 8 Kg/cm to about 35 Kg/cm and higher.

For the Gels to be considered useful for flossing, the gels, critically, should advantageously exhibit a propagating tension tear force (when a cylindrical sample is notched and a tear is initiated at the notched area and propagated past its maximum cylindrical diameter by length-wise stretching of the cylindrical sample) of at least about 1 Kg/cm, more advantageously at least 2 Kg/cm, and still more advantageously of about 4 Kg/cm and higher. The extreme tear resistant gels typically will exhibit even higher tension tear values.

RIGIDITY CRITERIA

The rigidities of the extreme tear resistant useful for flossing can advantageously range from about 350 gram to about 1,800 gram Bloom, more advantageously from about 400 gram to about 1,500 gram Bloom, especially more advantageously from about 450 gram to about 1,200 gram Bloom, still more advantageously from about 450 gram to about 1,000 gram Bloom, and less advantageously at values of greater than 1,800 gram Bloom.

HIGH STRESS RUPTURE CRITERIA

This is demonstrated by forming very soft gel samples, for example 100 parts copolymer to 800 parts plasticizing oil. The soft gel is made in a 16 mm×150 mm test tube, the gel cylinder is cut or notched at one point about its cross-section and gripped lengthwise tightly in the left hand about this cross-section point and a length of exposed gel is gripped lengthwise around the adjacent cross-section point tightly by the right hand as close to the left hand as possible without stretching. With the two hands gripping the gel sample's cross-section about the notched point, the hands are moved in opposite directions to tear apart the gel sample at the cross-section point. The high shearing action by the gripping hands is done at the fastest speed possible as can be performed by human hands. Using this demonstration, the crystal gels will not easily break or tear completely apart, whereas, amorphous S-EB-S and S-EP-S gels break or tears apart easily. Likewise the various crystal gels of the invention described herein are tested and found to be more resistant to high stress rupture than typical SEBS and SEPS gels. For floss, the improved resistance high stress rupture is essential.

In general, as a minimum, the flossing gels should exhibit several critical properties, including advantageously the ability to:

(1) withstand a shearing force of at least about 5 Kg under the string twisting test described above, (2) perform at least 4 flossing cycles without breaking apart when tested on a set of simulated upper front teeth fully contacting under a uniform spring load of two pound, (3) exhibit a tensile strength of at least 5 Kg/cm$^2$ and higher, (4) exhibit a propagating tear force at 180° U bend tear test of at least about 1 Kg/cm, and (5) exhibit a propagating tension tear force (on a notched cylindrical sample) of at least about 1 Kg/cm.

For use as a dental floss, the gel is made (by extruding, spinning, casting, etc) as a continuous gel strand, the gel strand can be in the shape of a fiber of a selected diameter (from less than about 0.15 to about 5.0 mm and greater) as a continuous tape having a selected width and thickness (less than 0.10 mm thin to about 5.0 mm and thicker) or in any desired shape suitable for flossing. The fiber, tape or a selected shape is then cut to a desired length, rolled up and placed into a dispenser suitable for containing and dispensing a measured use amount of gel floss. The continuous fiber and tape can be partly cut or notched for measured single or multiple use. When the floss is pulled from the dispenser to a point showing the notched or cut mark on the length of gel floss, the lid is pushed down on the gel floss nipping it and allowing the floss to be further pulled and separated at the notched or cut point. Additionally, a suitable floss dispenser containing a measured length of gel floss can be fitted with a cutting edge attached to its lid or on its body and the uncut and un-notched gel floss can be dispensed from the dispensing container and cut at the desired measured use length by pressing close the dispenser cutting edge down on the floss so as to nip and cut the gel or by simply closing the dispenser lid or running the gel along the cutting edge on the dispenser body separating a useful length of gel floss.

In practice, typically during flossing, a gel strand will under go various deformations, some of these deformations can be measured, including original shape, extended shape under tension, nipping force, and nipped deformation under a measured force and width. Typically, any shaped gel strand can be used for flossing, a square cross-section, a circular cross-section, a rectangular cross-section, round, oval, etc. For example, a 2.35 mm diameter strand when extended under a force of 2.5 kg can be nipped down to 0.14 mm thickness (along a 3 mm uniform width of its cross-section) by a force of 0.9072 Kg (2.0 pound force), a reduction of 16.78:1; a 1.89 mm diameter strand when extended under a force of 2.5 kg can be nipped down to 0.14 mm thickness by a force of 0.9072 Kg (2.0 pound force), a reduction of 13.5:1; a 2.75 mm diameter strand when extended under a force of 2.5 kg can be nipped down to 0.19 mm thickness by a force of 0.9072 Kg (2.0 pound force), a reduction of 14.4:1; and a 2.63 mm diameter strand when extended under a force of 2.5 kg can be nipped down to 0.19 mm thickness by a force of 0.9072 Kg (2.0 pound force), a reduction of 13.8:1, the cross-section of the gel floss can be reduced to any degree by stretching and nipping (from less than about 1% to about 1,600% and higher). Advantageously, a gel having the required strength, tear resistance, gel rigidity, and other characteristics described can be formed into a floss of any selected cross-section and thickness provided the floss is capable of being stretched when flossing under tension without breaking. Typically the stretching or pulling force is from about less than 0.1 Kg to about 3 Kg and higher. The cross-section of the strand of gel floss should be capable of being nipped by a 0.9027 Kg (2 pounds) force applied across a width of 3 mm from its original cross-sectional dimensions to a nipped thickness of about 3.0 mm to about 0.02 mm and lower, more advantageously from about 2.5 mm to about 0.04 mm and lower, still more advantageously from about 2.0 mm to about 0.08 mm and lower; especially advantageously from about 1.5 mm to about 0.15 mm and lower; especially more advantangeously from about 1.2 mm to about 0.20 mm and lower; especially still more advantageously from about 1.0 mm to about 0.25 mm and lower.

The gels made from higher viscosity copolymers (i) are resistant to breaking when sheared than triblock copolymer gels. This can be demonstrated by forming a very soft gel, for example 100 parts copolymer to 800 parts plasticizing oil. The soft gel is cut into a strip of 2.5 cm×2.5 cm cross-section, the gel strip is gripped lengthwise tightly in the left hand about its cross-section and an exposed part of the gel strip being gripped lengthwise around its cross-section tightly by the right hand as close to the left hand as possible without stretching. With the two hands gripping the gel strip's cross-section, the hands are moved in opposite directions to shear apart the gel strip at its cross-section. The shearing action by the gripping hands is done at the fastest speed possible as can be performed by human hands. The shearing action is performed at a fraction of a second, possible at about 0.5 seconds. Using this demonstration, the copolymer (I) gels will not easily break completely apart as would gels formed from triblock copolymers. In some cases, it will take two, three, or more attempts to shear a high viscosity copolymer (I) gel strip this way. Whereas, a lower viscosity triblock copolymer gel strip can be sheared apart on the first try. For gels made from copolymers with viscosities of 5 wt % solution in Toluene, their shear resistance will decrease with decreasing viscosity. For example, the shear strengths as tested by hand shearing described above of gels made from copolymers having viscosities of 150, 120, 110, 105, 95, 90, 89, 85, 70, 60, 58, 48, 42, 40, 35, 28, 27, 25, 21 cps, and the like can be expected to decrease with decreasing viscosity.

The tensile strengths of multiblock copolymer gels made from higher viscosity copolymers (I) can be slightly lower than or equal to the tensile strengths of gels made from lower solution viscosity triblock copolymers (II).

Strands of gels comprising higher viscosity multiblock copolymers will perform better than gel strands made from gels of lower viscosity triblock copolymers when used in flossing amalgam molars and more than three times better when used in flossing front teeth.

Gels, in general, will exhibit higher tensile and greater tear resistance than their parent gels containing higher concentrations of plasticizer.

As compared to spongy nylon, regular waxed nylon, and extra fine unwaxed nylon when flossing amalgam molars, the performance of multiblock copolymer gels are on the average substantially better.

While advantageous components and formulation ranges based on the desired properties of the multiblock copolymer gels nave been disclosed herein. Persons of skill in the art can extend these ranges using appropriate material according to the principles discussed herein. All such variations and deviations which rely on the teachings through which the present invention has advanced the art are considered to be within the spirit and scope of the present invention.

The invention is further illustrated by means of the following illustrative embodiments, which are given for purpose of illustration only and are not meant to limit the invention to the particular components and amounts disclosed.

EXAMPLE I

Gels of 100 parts of high viscosity linear Kraton G1651 (amorphous S-EB-S), Septon 8006 (amorphous S-EB-S), Kraton GRP6918 (SEPS) and a high viscosity radial amorphous midblock segment (SEB)$_n$ triblock copolymers and 800, 600, 500, 450, 300, 250 parts by weight of Duraprime 200 white oil (plasticizer) are melt blended and samples molded, the bulk gel rigidities are found to be within the range of 2 to 1,800 gram Bloom and the tensile strength, notched tear strength, and resistance to fatigue are found to decrease with increase amounts of plasticizers and unsuitable for use as floss.

EXAMPLE II

Gels of 100 parts of high viscosity linear (S-EB-S), (S-EP-S), (S-B-EP-S), (S-B-EB-S) (S-B-EP-B-S), (S-B-EB-B-S), (S-B-EB-EP-S), (S-B-EP-EB-S), (S-EB-EP-S), and (S-EP-B-EP-S) block copolymers and 800, 600, 500, 450, 300, 250 parts by weight of Duraprime 200 white oil (plasticizer) are each melt blended and samples molded, the bulk gel rigidities are found to be within the range of 2 to 1,800 gram Bloom and the tensile strength, notched tear strength, and resistance to fatigue are found to decrease with increase amounts of plasticizers and unsuitable for use as floss.

EXAMPLE III

Gels of 100 parts of high viscosity linear (S-EB$_{25}$-EP-S), (S-E-EB$_{25}$-S) (S-EP-E-EP-S), (S-E-EB-S), (S-E-EP-S), (S-E-EP-E-S), (S-E-EB-B-S), (S-E-EB-E-S), (S-E-B-EB-S), (S-E-B-EP-S), (S-E-EB-EP-S), (S-E-EP-EB-S), (S-E-EP-E-EP-S), (S-E-EP-E-EB-S), (S-E-EB-B-EP-S), (S-E-EP-B-EB-S), (S-E-EP-E-EP-E-S), (SE-EP-E-EB-S), (S-E-EP-E-EP-EB-S), (S-E-EP-E-EP-E-S), and (S-E-EP-EB-EP-EB-B-S) block copolymers and 800, 600, 500, 450, 300, 250 parts by weight of Duraprime 200 white oil (plasticizer) are each melt blended and samples molded, the bulk gel rigidities are found to be within the range of 2 to 1,800 gram Bloom and the tensile strength, notched tear strength, and resistance to fatigue and stress rupture are found to be greater than that of amorphous gels of Example II and suitable for use as floss.

EXAMPLE IV

Example III is repeated using plasticizers L-14, L-50, L-100, H-15, H-25, H-35, H-50, H-100, H-300, L-14E, H-300E, Actipol E6, E16, E23, Kraton L-1203, EKP-206, EKP-207, HPVM-2203, Amoco C-60, Piccolyte S10, Duraprime (55, 70, 90, 200, 350, 400), Tufflo (6006, 6016, 6016M, 6026, 6036, 6056, 6206) Bayol, Bernol, American, Blandol, Drakeol, Ervol, Gloria, and Kaydol, the bulk gel rigidities are found to be within the range of 2 gram to 1,800 gram Bloom and the tear resistance of the multiblock copolymers at corresponding rigidities are found to be substantially higher than the tear resistance of the triblock copolymer gels of EXAMPLES I or II.

EXAMPLE V

Example III is repeated using plasticizers L-14, L-50, L-100, H-15, H-25, H-35, H-50, H-100, H-300, L-14E, H-300E, Actipol E6, E16, E23, Kraton L-1203, EKP-206, EKP-207, HPVM-2203, Amoco C-60, Piccolyte S10, Duraprime (55, 70, 90, 200, 350, 400), Tufflo (6006, 6016, 6016M, 6026, 6036, 6056, 6206,) Bayol, Bernol, American, Blandol, Drakeol, Ervol, Gloria, and Kaydol, the bulk gel rigidities are found to be within the range of 2 gram to 1,800 gram Bloom and the tear resistance of the multiblock copolymers at corresponding rigidities are found to be substantially higher than the tear resistance of the triblock copolymer gels of EXAMPLE I or II.

EXAMPLE VI

A gel composition of 100 parts of Kuraray's S-E-EP-S 4055 copolymer and 400 parts by weight of Duraprime 200 white oil was made following Example I and extruded and drawn (from a 7.15 mm diameter orifice) into a strand of uniform diameter onto a take-up roll of continuous lengths. The strand diameter was varied by increasing and decreasing the speed of the take-up roll. The continuous strand of varying diameter gel strand was cut to suitable lengths for use and testing as dental floss. Additional gel was also casted in varying thickness and tested. The results of samples tested are shown in Table 3, #4–7; Table 4, #12–15 and 20; Table 5 #22, 23, 27–29; Table 6 #36–32; Table 7, #40–43, #76 and 77. Sample Nos. 76 and 77 were tested together. Sample 77 exhibited higher tensile strength after 27.75% of plasticizing oil was extracted (with 2.89 parts by weight of oil remaining), its rigidity remained substantially unchanged.

EXAMPLE VII

A gel composition of 100 parts of Kraton G1651 and 400 parts by weight of Duraprime 200 white oil was made following Example I and extruded and drawn (from a 7.15 mm diameter orifice) into a strand of uniform diameter onto a take-up roll of continuous lengths. The strand diameter was varied by increasing and decreasing the speed of the take-up roll. The continuous strand of varying diameter gel strand was cut to suitable lengths for use and testing as dental floss. Additional gel was also casted in varying thickness and tested. The results of samples tested are shown in Table 3B, #8–11; Table 4, #16–19 and 21; Table 5, #24–26; Table 6, #33–35; and Table 7, #36–39.

TABLE 3A

| | | Flossing Cycles to Break | | |
|---|---|---|---|---|
| Sample No. | Floss Type | cross-section size | [2]Floss amalgram molars to | [3]Floss fronts |
| 1 | [4]Unwaxed spongy nylon | 0.30 | 18 | 200+ |
| 2 | [5]Regular waxed nylon | 0.11 | 11 | 200+ |
| 3 | [6]Extra fine unwaxed nylon | 0.06 | 6 | 200+ |

TABLE 3B

| | | Flossing Cycles to Break | | |
|---|---|---|---|---|
| Sample No. | Floss Type | Relaxed/extended dia. (mm) | [2]Floss amalgram molars to break | [3]Floss fronts to |
| 4 | [7]Gel | 2.42/0.16 | 37 | 76 |
| 5 | [7]Gel | 2.63/0.17 | 29 | 83 |
| 6 | [7]Gel | 2.75/0.17 | 36 | 183 |
| 7 | [7]Gel | 2.83/0.20 | 20 | 74 |
| 8 | [8]Gel | 3.22/0.22 | 8 | 30 |
| 9 | [8]Gel | 2.48/0.31 | 4 | 20 |
| 10 | [8]Gel | 3.16/0.33 | 6 | 44 |
| 11 | [8]Gel | 2.86/0.24 | 5 | 29 |

[1]floss dimension relaxed state and when extended during flossing cycles. [2]Test conditions: number of flossing cycles (before breaking) between amalgam alloy metal (fully contacting) lower, left first and second human back molars. [3]Test conditions: number of flossing cycles (before breaking) between upper human front teeth. [4]Oral-B Ultra Floss™, interlocking network of spongy nylon floss. [5]Johnson & Johnson regular waxed nylon floss. [6]Johnson & Johnson extra fine unwaxed nylon floss. [7]Gel made from 100 parts by weight of S-E-EP-S 4055 multiblock copolymer having a Brookfield viscosity of 90 as measured for a 5 wt % solution in toluene at 30° C. and 400 parts by weight of Duraprime 200 plasticizing oil. [8]Gel made from 100 parts by weight of SEBS Kraton G1651 copolymer having a Brookfield viscosity of 40 as measured for a 5 wt % solution in toluene at 30° C. [2,3]Any selected test methods may be utilized in testing the floss performance of the gels. For example, a set of simulated upper front teeth fully contacting under a uniform spring load of two pounds may be used in place of human teeth. Such simulated testing conditions may be more severe than conditions 2 and less severe than conditions 3 above.

TABLE 4

Tensile Strength of Gel Strands

| Sample No. | Number of Strands | Radius (mm) | Area (cm$^2$) | Failure (Kg) | Tensile (Kg/cm$^2$) |
|---|---|---|---|---|---|
| 12 | 3 | 1.325 | 0.165 | 9.00 | 54.54 |
| 13 | 4 | 1.250 | 0.196 | 9.50 | 48.39 |
| 14 | 4 | 1.421 | 0.253 | 9.50 | 37.44 |
| 15 | 5 | 1.359 | 0.290 | 12.5 | 43.08 |
| 16 | 2 | 2.14 | 0.287 | 14.0 | 48.78 |
| 17 | 2 | 1.55 | 0.151 | 11.5 | 75.95 |
| 18 | 2 | 1.17 | 0.086 | 8.50 | 98.84 |
| 19 | 2 | 1.322 | 0.109 | 9.0 | 81.96 |
| 20 | 6 | 1.375 | 0.356 | 14 | 39.32 |
| 21 | 2 | 1.445 | 0.131 | 10 | 76.33 |
| 76 | 1 | 1.22 | 0.0467 | 2.00 | 42.82 |
| 77[†] | 1 | 1.38 | 0.0598 | 4.00 | 66.88 |

[†]Plasticizing oil extracted

TABLE 5

Tensilke Strength of Bulk Gels Samples

| Sample No. | Cross-section (cm2) | Failure (Kg) | Tensile (Kg/cm2) |
|---|---|---|---|
| 22 | 1.96 | 24.0 | 12.24 |
| 23 | 1.56 | 25.0 | 16.02 |
| 24 | 0.58 | 15.0 | 25.83 |
| 25 | 0.602 | 16.0 | 26.54 |
| 26 | 1.163 | 24.0 | 20.64 |
| 27 | 0.913 | 21.0 | 23.00 |
| 28 | 0.595 | 18.5 | 36.56 |
| 29 | 0.702 | 19.0 | 27.06 |

TABLE 6

180° U Bend Tear Propagation of Bulk Gels Samples

| Sample No. | Tear width (cm) | Failure (Kg) | Tear Force (Kg/cm) |
|---|---|---|---|
| 30 | 1.31 | 2.75 | 2.09 |
| 31 | 1.28 | 3.0 | 2.30 |
| 32 | 1.14 | 2.75 | 2.56 |
| 33 | 1.53 | 2.75 | 1.79 |
| 34 | 1.27 | 2.25 | 1.76 |
| 35 | 1.26 | 2.25 | 1.77 |

TABLE 7

Notched Gel Strand Tension Tear Propagation

| Sample No. | Strand Dia. (mm) | Failure (Kg) | Tear Force (Kg/cm) |
|---|---|---|---|
| 36 | 2.86 | 0.75 | 2.62 |
| 37 | 2.49 | 0.75 | 3.01 |
| 38 | 3.09 | 0.60 | 1.94 |

TABLE 7-continued

Notched Gel Strand Tension Tear Propagation

| Sample No. | Strand Dia. (mm) | Failure (Kg) | Tear Force (Kg/cm) |
|---|---|---|---|
| 39 | 2.62 | 0.70 | 2.67 |
| 40 | 2.54 | 0.60 | 2.36 |
| 41 | 1.94 | 1.10 | 5.67 |
| 42 | 1.58 | 0.75 | 4.74 |
| 43 | 2.34 | 1.2 | 5.12 |

The tensile strengths of gels made from higher viscosity copolymers are lower than the tensile strengths of gels made from lower solution viscosity copolymers. This was later found to be due to orientation effects and not considered significant.

The tear resistance of gels made from higher viscosity copolymers are higher than the tear resistance of gels made from lower solution viscosity copolymers.

Gel strands made from higher viscosity copolymers perform better than gel strands made of lower viscosity copolymers when used in flossing amalgam molars and more than three times better when used in flossing front teeth.

As compared to spongy nylon, regular waxed nylon, and extra fine unwaxed nylon when flossing amalgam molars, the performance of gels are on the average substantially better.

Examples below illustrate other modes of practice contemplated.

EXAMPLE VIII

Gels of 100 parts of linear high content butylene (S-EB-S) and high content isopropylethyene (S-EP-S) block copolymers and 800, 600, 500, 450, 300, 250 parts by weight of Duraprime 200 white oil (plasticizer) are each melt blended in admixture with the gels of Example III and samples molded, the bulk gel rigidities are found to be within the range of 2 to 1,800 gram Bloom and the tensile strength, notched tear strength, and resistance to fatigue and stress rupture are found to be greater than that of amorphous gels of Example II and suitable for use as floss.

The gels are especially advantageously useful when subjected to conditions of stretching, shearing, and tearing during flossing. The gels useful for flossing are characterized by low rigidities and high solution viscosity of the gels made from multiblock copolymers having two or more midblock polymer chains.

Tables 8–10 are illustrative in meeting one or more of the criteria detailed above.

8. Illustrative Modes of Practice Contemplated for multiblock copolymer Gels

| 100 Parts by wt | 5 Wt % Copolymer Viscosity (cps) | Styrene % | Parts by Wt of Oil | Number of floss cycles to break | Sample No. |
|---|---|---|---|---|---|
| S-E-EP-S | 90 | 30 | 300 | 30+ | 44 |
| S-E-EP-E-S | 60 | 30 | 300 | 30+ | 45 |
| (S-E-EP)n | 240 | 35 | 300 | 30+ | 46 |
| (S-E-EP-E)n | 240 | 35 | 300 | 30+ | 47 |
| S-B-EP-S | 90 | 30 | 300 | 30+ | 48 |
| S-E-EB-S | 90 | 35 | 300 | 30+ | 49 |
| S-EB-EP-S | 90 | 30 | 300 | 30+ | 50 |
| S-E-EP-EP-S | 90 | 30 | 300 | 30+ | 51 |

TABLE 9

Illustrative Modes of Practice Contemplated for multiblock copolymer Gels

| 100 Parts by wt | Wt % Copolymer Viscosity (cps) | Styrene % | Parts by Wt of Oil | Number Floss cycles to Break | Sample No. |
|---|---|---|---|---|---|
| S-E-EP-EB-S | 120 | 33 | 250 | 30+ | 52 |
| S-E-EP-EP-S | 120 | 33 | 250 | 30+ | 53 |
| (S-B-EP)n | 380 | 35 | 250 | 30+ | 54 |
| (S-E-EB)n | 380 | 35 | 250 | 30+ | 55 |
| S-E-EP-E-EP-S | 120 | 30 | 250 | 30+ | 56 |
| S-E-EP-P-S | 120 | 35 | 250 | 30+ | 57 |
| S-E-B-EP-S | 120 | 30 | 250 | 30+ | 58 |
| S-E-EP-EP-E-S | 120 | 30 | 250 | 30+ | 59 |

TABLE 10

Illustrative Modes of Practice Contemplated for multiblock copolymer (0.5–2.0 cm diameters) Gel Strands

| 100 Parts by wt | 5 Wt % Copolymer Viscosity (cps) | Styrene % | Parts by Wt of Oil | # Floss cycles to Break | Sample No. |
|---|---|---|---|---|---|
| S-E-EP-S | 40 | 30 | 350 | 30+ | 60 |
| S-E-EP-S | 60 | 30 | 350 | 30+ | 61 |
| (S-E-EP-EB)n | 340 | 30 | 350 | 30+ | 62 |
| (S-E-EP-EP-E)n | 340 | 30 | 350 | 30+ | 63 |
| S-E-EP-E-EP-E-S | 90 | 30 | 350 | 30+ | 64 |
| S-EB-EP-EP-S | 90 | 35 | 350 | 30+ | 65 |
| S-B-EB-B-S | 90 | 30 | 350 | 30+ | 66 |
| S-E-EP-EP-E-S | 90 | 30 | 350 | 30+ | 67 |

While certain features of this invention have been described in detail with respect to various embodiments thereof, it will, of course, be apparent that other modifications can be made within the spirit and scope of this invention, and it is not intended to limit the invention to the exact details shown above except insofar as they are defined in the following claims.

What I claim is:

1. An improved dental floss comprising: a soft, flexible, high strength, high tear resistant, and high stress rupture resistant crystal gel, in the shape of a strand, a thread, a strip, a band, a yarn, a tape, or a sheet of film for flossing teeth, said sheet having a selected shaped peripheral edge of selective thickness and at least two holes positioned at a selected distance apart through said film and at a selective distance away from said edge, each of said holes being a size suitable for insertion therethrough by one or more fingers of one or both hands for positioning said fingers through said film without substantial constriction of blood flow in said fingers; said holes with said fingers therethrough by allowing said fingers to manipulate said film and said shaped peripheral edge for:

a) providing opposing inserted fingers of each hand to extend substantially taught a major lengths of said shaped peripheral edge by opposing inserted fingers pulling in opposite direction;

b) providing freedom of one or more fingers including thumbs and forefingers of one or both of said hands to grip, pull, push, deform, guide, fold or otherwise manipulate a length of said shaped peripheral edge between said teeth during flossing;

c) said sheet about said shaped peripheral edge suitable of being: extended taught for flossing) said teeth having a tight teeth gap, or folded into a thicker extended film layer for flossing said teeth having a wide or loose teeth gap; said crystal gel comprising:

(I) 100 parts by weight of one or more linear, branched, radial, star-shaped, multi-arm or branched block copolymers or mixtures of two or more said block copolymers, said copolymers having at least one substantially crystalline polyethylene midblocks, (II) selected amounts of a plasticizing oil sufficient to achieve a gel rigidity of about 2 gram Bloom to about 1,800 gram Bloom, said (I) copolymers in combination with or without a selected amount of (III) one or more of a selected polymer, copolymer or resin, and when said (I) copolymers comprises one midblock, said (I) copolymer is of the formula comprising (i): poly(styrene-ethylene-styrene) or poly(styrene-ethylene)$_n$, or when said (I) copolymer comprises two or more midblocks, said (I) copolymer is of the formula comprising (ii): poly(styrene-ethylene-ethylene-propylene-styrene), poly(styrene-ethylene-ethylene-butylene-styrene), poly(styrene-ethylene-ethylene-popylene-ethylene-butylene-styrene-poly(styrene-ethylene-ethylene-propylene-ethylene-styrene), poly(styrene-ethylene-ethylene-propylene-ethylene-ethylene-proplene-ethylene-styrene), poly(styrene-ethylene-ethylene-butylene)$_n$, poly(styrene-ethylene-ethylene-propylene)$_n$, poly(styrene-ethylene-ethylene-propylene-ethylene)$_n$, poly(styrene-ethylene-ethylene-propylene-ethylene-ethylene-propylene)$_n$, or poly(styrene-ethylene-ethylene-propylene-ethylene-ethylene-propylene-ethylene)$_n$, wherein n is a number greater than two; said crystalline polyethylene midblocks being formed from hydrogenation of sufficient amounts of 1,4 poly(butadiene) midblocks which is capable of exhibiting a melting endotherm in differential scanning calorimeter curves of about 20° C. to about 75° C.; with the proviso that when said gel comprises one or more (i) copolymers, said gel is a mixture of (i) copolymers in combination with one or more (ii) copolymers or with one or more substantially amorphous midblock block copolymers: said (III) polymer, copolymer, or resin being poly(styrene-butadiene-styrene), poly(styrene-butadienel, poly(styrene-isoprene-styrene), poly-styrene-isoprene), poly(styrene-ethylene-propylene), poly(styrene-ethylene-propylene-styrene), poly(styrene-ethylene-butylene-styrene), low viscosity poly(styrene-ethylene-butylene-styrene), poly(styrene-ethylene-butylene), poly(styrene-ethylene-propylene)n, poly(styrene-ethylene-butylene)n, polystyrene, polybutylene, poly(ethylene-propylene), poly(ethylene-butylene), polypropylene, polyethylene, polymerized mixed olefins, polyterpene, glycerol ester of rosin, pentaerythritol ester of rosin, saturated alicyclic hydrocarbon, coumarone indene, hydrocarbon, mixed olefin, alkylated aromatic hydrocarbon polyalphamethylstyrene/vinyl toluene copolymer, or a low viscosity polystyrene; wherein said selected copolymer is a linear, branched or star-shaped, or multiarm copolymer.

2. A floss according to claim 1, wherein said crystal gel is capable of exhibiting a melting endotherm in differential scanning calorimeter, DSC, curves of about 25° C. to about 80° C.

3. A floss comprising: a soft, flexible, high strength, high tear resistant, and high stress rupture resistant crystal gel in the shape of a strand, a thread, a strip, a band, a yarn, a tape, or a sheet of film for flossing teeth and massaging gums which is non-lacerating to the gums and having a softness as determined by gel rigidity substantially matching the rigidity of said gums, said crystal gel made from one or more block copolymers having one or more crystalline polyethylene midblocks which copolymer is capable of exhibiting a melting endotherm as determined by differential scanning calorimeter curves of about 20° C. to about 75° C.

4. A floss comprising: a soft, flexible, high strength, high tear resistant, and high stress rupture resistant crystal gel in the shape of a strand, a tape, or a sheet of film for flossing teeth and massaging gums which is non-lacerating to the gums and having a softness as determined by gel rigidity less than the rigidity of said gums, said crystal gel made from one or more block copolymers having one or more crystalline polyethylene midblocks which copolymer is capable of exhibiting a melting endotherm as determined by differential scanning calorimeter curves of about 20° C. to about 75° C.

5. A floss comprising: a soft, flexible, high strength, high tear resistant, and high stress rupture resistant crystal gel in the shape of a strand, a tape, or a sheet of film for flossing teeth and massaging gums which is non-lacerating to the gums and having a softness as determined by gel rigidity not substantially greater than the rigidity of said gums, said crystal gel made from one or more block copolymers having one or more crystalline polyethylene midblocks which copolymer is capable of exhibiting a melting endotherm as determined by differential scanning calorimeter curves of about 20° C. to about 75° C.

6. A floss comprising: a soft and flexible crystal gel in the shape of a strand, a tape, or a sheet of film for flossing teeth and massaging gums which exhibits higher tensile strength, higher tear resistance, or higher stress rupture resistance than gels made from amorphous styrene-ethylene-butylene-styrene or styrene-ethylene/propylene-styrene block copolymers, said crystal gel made from one or more block copolymers having one or more crystalline polyethylene midblocks which copolymer is capable of exhibiting a melting endotherm as determined by differential scanning calorimeter curves of about 20° C. to about 75° C.

7. A floss comprising: a soft and flexible crystal gel in the shape of a strand, a thread, a strip, a band, a yarn, a tape, or a sheet of film for flossing teeth and massaging gums which exhibits higher tear resistance as determined by a higher flossing cycles to break than gels made from amorphous styrene-ethylene-butylene-styrene or styrene-ethylene/propylene-styrene block copolymers, said crystal gel made from one or more block copolymers having one or more crystalline polyethylene midblocks which copolymer is capable of exhibiting a melting endotherm as determined by differential scanning calorimeter curves of about 20° C. to about 75° C.

8. A floss comprising: a soft and flexible crystal gel in the shape of a strand, a thread, a strip, a band, a yarn, a tape, or a sheet of film for flossing teeth and massaging gums which exhibits higher stress rupture resistance as determined by a higher flossing cycles to break than gels made from amorphous styrene-ethylene-butylene-styrene or styrene-ethylene/propylene-styrene block copolymers, said crystal gel made from one or more block copolymers having one or more crystalline polyethylene midblocks which copolymer is capable of exhibiting a melting endotherm as determined by differential scanning calorimeter curves of about 20° C. to about 75° C.

9. A crystal gel comprising:
(I) 100 parts by weight of one or more linear, branched, radial, star-shaped, multi-arm or branched block copolymers or mixtures of two or more said copolymers, said copolymers having at least one substantially crystalline polyethylene midblocks,
(II) a selected amounts of a plasticizing oil sufficient to achieve a gel rigidity of about 2 gram Bloom to about 1,800 gram Bloom, said (I) copolymers in combination with or without a selected amount of
(III) one or more of a selected polymer, copolymer or resin, and
when said (I) copolymers comprises one midblock, said copolymer is of the formula comprising (i): poly(styrene-ethylene-styrene) or poly(styrene-ethylene)$_n$, or
when said (I) copolymer comprises two or more midblocks, said copolymer is of the formula comprising (ii): poly(styrene-ethylene-ethylene-propylene-styrene), poly(styrene-ethylene-ethylene-butylene-styrene), poly(styrene-ethylene-ethylene-popylene-ethylene-butylene-styrene), poly(styrene-ethylene-ethylene-propylene-ethylene-styrene), poly(styrene-ethylene-ethylene-propylene-ethylene-ethylene-propylene-ethylene-styrene), poly(styrene-ethylene-ethylene-butylene)$_n$, poly(styrene-ethylene-ethylene-propylene)$_n$, poly(styrene-ethylene-ethylene-propylene-ethylene)$_n$, poly(styrene-ethylene-ethylene-propylene-ethylene-ethylene-propylene)$_n$, or poly(styrene-ethylene-ethylene-propylene-ethylene-ethylene-propylene-ethylene)$_n$, wherein n is a number greater than two; said crystalline polyethylene midblocks being formed from hydrogenation of sufficient amounts of 1,4 poly(butadiene) midblocks which is capable of exhibiting a melting endotherm in differential scanning calorimeter curves of about 20° C. to about 75° C.; with the proviso that when said gel comprises one or more (i) copolymers, said gel is a mixture of (i) copolymers in combination with one or more (ii) copolymers or with one or more substantially amorphous midblock block copolymers; said (III) polymer, copolymer, or resin being poly(styrene-butadiene-styrene), poly(styrene-butadiene), poly(styrene-isoprene-styrene), poly(styrene-isoprene), poly(styrene-ethylene-propylene), poly(styrene-ethylene-propylene-styrene), poly(styrene-ethylene-butylene-styrene), low viscosity poly(styrene-ethylene-butylene-styrene), poly(styrene-ethylene-butylene), poly(styrene-ethylene-propylene)n, poly(styrene-ethylene-butylene)n, polystyrene, polybutylene, poly(ethylene-propylene), poly(ethylene-butylene), polypropylene, polyethylene, polymerized mixed olefins, polyterpene, glycerol ester of rosin, pentaerythritol ester of rosin, saturated alicyclic hydrocarbon, coumarone indene, hydrocarbon, mixed olefin, alkylated aromatic hydrocarbon, polyalphamethylstyrene/vinyl toluene copolymer, or a low viscosity polystyrene; wherein said selected copolymer is a linear, branched or star-shaped, or multiarm copolymer.

10. A crystal gel of claim 9 in the form of a thread, a tape, a band, a yarn, or a sheet of film.

11. A crystal gel of claim 9 in the form of a thread, a tape, a band, a yarn, or a sheet of film; wherein said gel having a gel rigidity of greater than 1,800 gram Bloom.

12. A crystal gel comprising:
(I) 100 parts by weight of one or more linear, branched, radial, star-shaped, multi-arm or branched block copolymers or mixtures of two or more said copolymers, said copolymers having at least one substantially crystalline polyethylene midblocks,
(II) a selected amounts of a plasticizing oil sufficient to achieve a gel rigidity of about 2 gram Bloom to about 1,800 gram Bloom; said (I) copolymers in combination with or without a selected amount of
(III) one or more of a selected polymer, copolymer or resin, and
when said (I) copolymers comprises one midblock, said copolymer is of the formula comprising (i): poly(styrene-ethylene-styrene) or poly(styrene-ethylene)$_n$, or
when said (I) copolymer comprises two or more midblocks, said copolymer is of the formula comprising (ii): poly(styrene-ethylene-ethylene-butylene-styrene), poly(styrene-ethylene-ethylene-popylene-ethylene-butylene-styrene), poly(styrene-ethylene-ethylene-propylene-ethylene-styrene), poly(styrene-ethylene-ethylene-propylene-ethylene-ethylene-propylene-ethylene-styrene), poly(styrene-ethylene-ethylene-butylene)$_n$, poly(styrene-ethylene-ethylene-propylene)$_n$, poly(styrene-ethylene-ethylene-propylene-ethylene)$_n$, poly(styrene-ethylene-ethylene-propylene-ethylene-ethylene-propylene)$_n$, or poly(styrene-ethylene-ethylene-propylene-ethylene-ethylene-propylene-ethylene)$_n$, wherein n is a number greater than two; said crystalline polyethylene midblocks being formed from hydrogenation of sufficient amounts of 1,4 poly(butadiene) midblocks which is capable of exhibiting a melting endotherm in differential scanning calorimeter curves of about 20° C. to about 75° C.; with the proviso that when said gel comprises one or more (i) copolymers, said gel is a mixture of (i) copolymers in combination with one or more (ii) copolymers or with one or more substantially amorphous midblock block copolymers; said (III) polymer, copolymer, or resin being poly(styrene-butadiene-styrene), poly(styrene-butadiene), poly(styrene-isoprene-styrene), poly(styrene-isoprene), poly(styrene-ethylene-propylene), poly(styrene-ethylene-propylene-styrene), poly(styrene-ethylene-butylene-styrene), low viscosity poly(styrene-ethylene-butylene-styrene), poly(styrene-ethylene-butylene), poly(styrene-ethylene-propylene)n, poly(styrene-ethylene-butylene)n, polystyrene, polybutylene, poly(ethylene-propylene), poly(ethylene-butylene), polypropylene, polyethylene, polymerized mixed olefins, polyterpene, glycerol ester of rosin, pentaerytritol ester of rosin, saturated alicyclic hydrocarbon, coumarone indene, hydrocarbon, mixed olefin, alkylated aromatic hydrocarbon, polyalphamethylstyrene/vinyl toluene copolymer, or a low viscosity polystyrene; wherein said selected copolymer is a linear, branched or star-shaped, or multiarm copolymer.

13. A crystal gel of claim 12 in the form of a thread, a tape, a band, a yarn, or a sheet of film.

14. A crystal gel of claim 12 in the form of a thread, a tape, a band, a yarn, or a sheet of film; wherein said gel having a gel rigidity of greater than 1,800 gram Bloom.

* * * * *